US010702583B2

(12) United States Patent
Murray

(10) Patent No.: US 10,702,583 B2
(45) Date of Patent: Jul. 7, 2020

(54) TREATMENT METHODS FOR AUTOIMMUNE DISORDERS

(75) Inventor: Lynne Anne Murray, King of Prussia, PA (US)

(73) Assignee: Promedior, Inc., Lexington, MA (US)

(*) Notice: Subject to any disclaimer, the term of this patent is extended or adjusted under 35 U.S.C. 154(b) by 217 days.

(21) Appl. No.: 12/720,845

(22) Filed: Mar. 10, 2010

(65) Prior Publication Data
US 2010/0260781 A1 Oct. 14, 2010

Related U.S. Application Data

(60) Provisional application No. 61/209,845, filed on Mar. 11, 2009.

(51) Int. Cl.
A61K 38/00 (2006.01)
C07K 14/00 (2006.01)
A61K 38/18 (2006.01)
A61K 38/17 (2006.01)
C12N 5/0783 (2010.01)
C12N 5/078 (2010.01)
A61K 38/20 (2006.01)
A61K 35/12 (2015.01)

(52) U.S. Cl.
CPC ...... A61K 38/1841 (2013.01); A61K 38/1716 (2013.01); A61K 38/20 (2013.01); C12N 5/0637 (2013.01); C12N 5/0648 (2013.01); A61K 2035/122 (2013.01); C12N 2501/998 (2013.01)

(58) Field of Classification Search
None
See application file for complete search history.

(56) References Cited

U.S. PATENT DOCUMENTS

| 4,233,969 A | 11/1980 | Lock et al. |
| 4,556,056 A | 12/1985 | Fischer et al. |
| 4,782,014 A | 11/1988 | Serban et al. |
| 5,092,876 A | 3/1992 | Dhawan et al. |
| 5,272,258 A | 12/1993 | Siegel et al. |
| 5,591,709 A | 1/1997 | Lindenbaum |
| 5,654,186 A | 8/1997 | Cerami et al. |
| 5,698,589 A | 12/1997 | Allen |
| 5,750,345 A | 5/1998 | Bowie |
| 5,804,446 A | 9/1998 | Cerami et al. |
| 5,846,796 A | 12/1998 | Cerami et al. |
| 5,989,811 A | 11/1999 | Veltri et al. |
| 6,037,458 A | 3/2000 | Hirai et al. |
| 6,054,121 A | 4/2000 | Cerami et al. |
| 6,071,517 A | 6/2000 | Fanger et al. |
| 6,126,918 A | 10/2000 | Pepys et al. |
| 6,174,526 B1 | 1/2001 | Cerami et al. |
| 6,365,570 B1 | 4/2002 | Van Kessel et al. |
| 6,406,698 B1 | 6/2002 | Svehang et al. |
| 6,537,811 B1 | 3/2003 | Freier |
| 6,600,019 B2 | 7/2003 | Prayaga et al. |
| 6,660,843 B1 | 12/2003 | Feige et al. |
| 6,872,541 B2 | 3/2005 | Mills |
| 7,666,432 B2 | 2/2010 | Gomer et al. |
| 7,763,256 B2 | 7/2010 | Gomer et al. |
| 8,012,472 B2 | 9/2011 | Gomer et al. |
| 8,057,802 B2 | 11/2011 | Gomer et al. |
| 8,187,599 B2 | 5/2012 | Gomer et al. |
| 8,187,608 B2 | 5/2012 | Gomer et al. |
| 8,247,370 B2 | 8/2012 | Pelura |
| 8,329,659 B2 | 12/2012 | Willett |
| 8,497,243 B2 | 7/2013 | Hesson et al. |
| 2002/0058284 A1 | 5/2002 | Winkel |
| 2003/0003567 A1 | 1/2003 | Barber et al. |
| 2003/0022245 A1 | 1/2003 | Mills |
| 2003/0162180 A1 | 8/2003 | Pricop |
| 2004/0068095 A1 | 4/2004 | Shimkets et al. |
| 2004/0121343 A1 | 6/2004 | Buechler et al. |
| 2005/0182042 A1 | 8/2005 | Feldman et al. |
| 2005/0238620 A1 | 10/2005 | Gomer et al. |
| 2007/0048855 A1 | 3/2007 | Gamez et al. |
| 2007/0065368 A1 | 3/2007 | Gomer et al. |
| 2009/0074754 A1 | 3/2009 | Hesson et al. |
| 2009/0202520 A1 | 8/2009 | Lupher, Jr. et al. |
| 2010/0111898 A1 | 5/2010 | Pelura |
| 2010/0266578 A1 | 10/2010 | Murray |
| 2010/0317596 A1 | 12/2010 | Willett et al. |
| 2010/0323970 A1 | 12/2010 | Willett |

FOREIGN PATENT DOCUMENTS

| EP | 0 206 302 A2 | 12/1986 |
| EP | 1 090 630 A1 | 4/2001 |
| JP | 11319542 A | 11/1999 |
| WO | WO 92/21364 A1 | 12/1992 |

(Continued)

OTHER PUBLICATIONS

Schrader et al. Animal models of dry eye. Developments in ophthalmology, Abstract. vol. 41, pp. 298-312 (2008).*
Barabino et al. Animal Models of Dry Eye: A Critical Assessment of Opportunities and Limitations. Investigative Ophthalmology & Visual Science, vol. 45, No. 6, pp. 1641-1646 (Jun. 2004).*
Brasil et al. Tear film analysis and its relation with palpebral fissure height and exophthalmos in Graves' ophthalmopathy. Arquivos Brasileiros de Oftalmologia, Abstract. vol. 68, No. 5, pp. 615-618 (Sep. 2005).*
Samarasinghe et al. A comparison between intratracheal and inhalation delivery of Aspergillus fumigatus conidia in the development of fungal allergic asthma in C57BL/6 mice. Fungal Biology 115:21-29 (2011).*
Sen et al. Structural, quantitative and functional comparison of amyloid P component in sera from patients with system lupus erythematosus and healthy donors, Scandinavian Journal of Immunology, 56:645-651 (2002).*

(Continued)

Primary Examiner — Elizabeth C. Kemmerer
Assistant Examiner — Regina M DeBerry
(74) Attorney, Agent, or Firm — Morse, Barnes-Brown & Pendleton, P.C.; Lisa M. Warren, Esq.

(57) ABSTRACT

The present invention provides methods and compositions for expanding T regulatory cells ex vivo or in vivo using one or more SAP agonists. The methods and compositions are useful in the treatment of autoimmune diseases and in preventing foreign graft rejection.

3 Claims, 9 Drawing Sheets

Specification includes a Sequence Listing.

(56) References Cited

FOREIGN PATENT DOCUMENTS

| WO | WO 94/27640 A1 | 12/1994 | | |
|---|---|---|---|---|
| WO | WO 95/05394 A1 | 2/1995 | | |
| WO | WO 95/33454 A1 | 12/1995 | | |
| WO | WO 97/16568 A1 | 5/1997 | | |
| WO | WO 97/26906 A1 | 7/1997 | | |
| WO | WO 99/41285 A1 | 8/1999 | | |
| WO | WO 99/45900 A1 | 9/1999 | | |
| WO | WO 01/74300 A1 | 10/2001 | | |
| WO | WO 03/031572 A2 | 4/2003 | | |
| WO | WO 03/097104 A1 | 11/2003 | | |
| WO | WO 2004/009823 A1 | 1/2004 | | |
| WO | WO 2004/016750 A2 | 2/2004 | | |
| WO | WO 2004/058292 A2 | 7/2004 | | |
| WO | WO 2004/059293 A2 | 7/2004 | | |
| WO | WO 2004/059318 A2 | 7/2004 | | |
| WO | WO 2004/076486 A1 | 9/2004 | | |
| WO | WO 2005/110474 A2 | 11/2005 | | |
| WO | WO 2005/115452 A2 | 12/2005 | | |
| WO | WO 2006/002438 A2 | 1/2006 | | |
| WO | WO 2006/002930 A2 | 1/2006 | | |
| WO | WO 2006/028956 | * | 3/2006 | ............ A61K 38/00 |
| WO | WO 2006/028956 A2 | 3/2006 | | |
| WO | WO 2006/039418 A2 | 4/2006 | | |
| WO | WO 2007/047207 A2 | 4/2007 | | |
| WO | WO 2007/047796 A2 | 4/2007 | | |
| WO | WO 2008/070117 A1 | 6/2008 | | |
| WO | WO 2009/009019 A2 | 1/2009 | | |
| WO | WO 2009/009034 A2 | 1/2009 | | |
| WO | WO 2010/104959 A1 | 9/2010 | | |
| WO | WO 2010/104961 A1 | 9/2010 | | |
| WO | WO 2010/115032 A1 | 10/2010 | | |
| WO | WO 2010/141918 A1 | 12/2010 | | |

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Bayston et al. Sequential measurement of the murine acute phase protein serum amyloid P component (SAP) as an indicator graft-versus-host disease following allogenic bone marrow transplantation in mice. Clin. Exp. Immunology vol. 81:329-333 (1990). (Year: 1990).*
Justice et al. Using the mouse to model human disease:increasing validity and reproducibility. Disease Models & Mechanisms vol. 9:101-103 (2016) (Year: 2016).*
Abe, R., et al., "Peripheral Blood Fibrocytes: Differentiation Pathway and Migration to Wound Sites," The Journal of Immunology, 166(12):7556-7562 (2001).
Agostini, et al., "Chemokine/Cytokine Cocktail in Idiopathic Pulmonary Fibrosis," Proc. Am. Thorac. Soc., 3(4):357-363 (2006).
Aiba, S., et al., "Immunoglobulin-Producing Cells in Plasma Cell Orificial Mucositis," Journal of Cutaneous Pathology, 16(4):207-210 (1989).
Alles, V. V., et al., "Inducible expression of PTX3, a new member of the pentraxin family, in human mononuclear phagocytes," Blood, 84(10):3483-3493 (1994).
Ashcroft, T., et al., "Simple Method of Estimating Severity of Pulmonary Fibrosis on a Numerical Scale," J Clin Pathol, 41(4):467-470 (1988).
Ashikawa, K., et al., "Piceatannol Inhibits TNF-Induced NF-κB Activation and NF-κB-Mediated Gene Expression Through Suppression of IκBα Kinase and p65 Phosphorylation," The Journal of Immunology, 169(11):6490-6497 (2002).
Bain, J., et al., "The Specificities of Protein Kinase Inhibitors: An Update," Biochem. J, 371(Pt 1):199-204 (2003).
Barna, B. P., et al., "Activation of Human Monocyte Tumoricidal Activity by C-Reactive Protein," Cancer Research, 47(5):3959-3963 (1987).

Bharadwaj, D., et al., "The Major Receptor for C-Reactive Protein on Leukocytes Is Fcγ Receptor II," The Journal of Experimental Medicine, 190(4):585-590 (1999).
Bickerstaff, M. C. M., et al., "Serum Amyloid P Component Controls Chromatin Degradation and Prevents Antinuclear Autoimmunity," Nature Medicine, 5(6):694-697 (1999).
Bodman-Smith, K. B., et al., "C-Reactive Protein-Mediated Phagocytosis and Phospholipase D Signalling Through the High-Affinity Receptor for Immunoglobulin G (FcγRI)," The Journal of Immunology, 107(2):252-260 (2002).
Booth, D. R., et al., Analysis of autoaggregation and ligand binding sites of serum amyloid P component by in vitro mutagenesis. From Amyloid & Amyloidosis 1998: Proceedings of the VIIIth International Symposium on Amyloidosis, Rochester, MN, pp. 23-25 (Aug. 7-11, 1998).
Brown, E. J., "The Role of Extracellular Matrix Proteins in the Control of Phagocytosis," Journal of Leukocyte Biology, 39(5):579-591 (1986).
Brown, M. R., et al., "Receptor-Ligand Interactions Between Serum Amyloid P Component and Model Soluble Immune Complexes," The Journal of Immunology, 151(4):2087-2095 (1993).
Bucala, R., et al., "Circulating Fibrocytes Define a New Leukocyte Subpopulation That Mediates Tissue Repair," Molecular Medicine, 1(1):71-81 (1994).
Cappiello, M. G., et al., "Suppression of IL-12 Transcription in Macrophages Following Fcγ Receptor Ligation," The Journal of Immunology, 166(7):4498-4506 (2001).
Castaño, A. P., et al., "Serum Amyloid P Inhibits Fibrosis Through FcγR-Dependent Monocyte-Macrophage Regulation in Vivo," Sci. Transl. Med. 1(5):1-26 (2009).
Chatziantoniou, et al., "Is Kidney Injury a Reversible Process," Curr. Opin. Nephrol. Hypertension, 17(1):76-81 (2008).
Chen, J., et al., "Platelet FcγRIIA His131Arg Polymorphism and Platelet Function: Antibodies to Platelet-Bound Fibrinogen Induce Platelet Activation," Journal of Thrombosis and Haemostasis, 1(2):355-362 (2003).
Chesney, J., et al., "Peripheral Blood Fibrocytes: Mesenchymal Precursor Cells and the Pathogenesis of Fibrosis," Curr. Rheumatology Reports, 2(6):501-505 (2000).
Chesney, J., et al., "Regulated Production of Type I Collagen and Inflammatory Cytokines by Peripheral Blood Fibrocytes," The Journal of Immunology, 160(1):419-425 (1998).
Chesney, J., et al., "The Peripheral Blood Fibrocyte is a Potent Antigen-Presenting Cell Capable of Priming Naive T Cells in Situ," Journal of Immunology, 94(12):6307-6312 (1997).
Chi, M., et al., "C-Reactive Protein Induces Signaling Through FcγRIIa on HL-60 Granulocytes," The Journal of Immunology, 168:1413-1418 (2002).
Christner, R. B., et al., "Binding of Human Serum Amyloid P-Component to Phosphocholine", Archives of Biochemistry and Biophysics, 314(2):337-343 (1994).
Clark, R. A. F., "Fibrin and Wound Healing," Annals New York Academy of Sciences 936:355-367 (2001).
Crouch, E., "Pathobiology of Pulmonary Fibrosis," Am J Physiol Lung Cell Mol Physiol, 259(4 Pt 1):L159-L184 (1990).
D'Andrea, A., et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production," J Exp Med, 181(2):537-546 (1995).
Daëron, M., "Fc Receptor Biology," Annual Review of Immunology 15:203-234 (1997).
Daëron, M., "Structural Bases of FcγR Functions," Int Rev Immunol. 16(1-2):1-27 (1997).
De Beer, F. C., et al., "Fibronectin and C4-Binding Protein are Selectively Bound by Aggregated Amyloid Component", J Exp Med., 154(4):1134-1149 (1981).
De Beer, F. C., et al., "Isolation and Characterization of C-Reactive Protein and Serum Amyloid P Component in the Rat," Immunology 45(1):55-70 (1982).
De Beer, F. C., et al., "Isolation of Human C-Reactive Protein and serum Amyloid P Component," Journal of Immunological Methods, 50(1):17-31 (1982).

(56) References Cited

OTHER PUBLICATIONS

De Haas, C. J. C., et al., "A Synthetic Lipopolysaccharide-Binding Peptide Based on Amino Acids 27-39 of Serum Amyloid P Component Inhibits Lipopolysaccharide-Induced Responses in Human Blood," The Journal of Immunology, 161(7):3607-3615 (1998).
De Paepe, et al., "Hydrogels Based on Agarose and Agarose/Gelatin Blends", International Journal of Artificial Organs, vol. 24, No. 8, p. 543, XP009108972 and XXVIII Congress of the European Society for Artificial Organs on Bridging the Interdisciplinarity; Gent, Belgium; Sep. 22-25, 2001.
Du Clos, T. W., "C-Reactive Protein Reacts With the U1 Small Nuclear Ribonucleoprotein," The Journal of Immunology, 143(8):2553-2559 (1989).
Du Clos, T. W., et al., "Reply to Human C-reactive protein does not bind to FcγRIIa on phagocytic cells," The Journal of Clinical Investigation, vol. 107(5):643 (2001).
Duchemin, A. M., et al., "Association of Non-Receptor Protein Tyrosine Kinases with the FcγRI/γ-Chain Complex in Monocytic Cells," The Journal of Immunology, 158(2):865-871 (1997).
Duckworth, et al., "The Structure of Agar Part I. Fractionation of a Complex Mixture of Polysaccharides," Carbohydrate Research, 16:189-197 (1971).
Emsley, J., et al., "Structure of Pentameric Human Serum Amyloid P Component," Nature 367(6461):338-345 (1994).
Flesch, B. K., et al., "The FCGR2A-Arg131 Variant is no Major Mortality Factor in the Elderly—Evidence From a German Centenarian Study," International Journal of Immunogenetics, 33(4):277-279 (2006).
Garden, A. S., et al., "Head and Neck Radiation and Mucositis," 1(1):30-34 (2007).
Gehring, et al., "Effect of Topically Applied Dexpanthenol on Epidermal Barrier Function and Stratum Corneum Hydration," Arzneim-Forsch./Drug Res., 50(11):659-663 (2000).
Gerhard, et al., "The Status, Quality and Expansion of the NIH Full-Length cDNA Project: The Mammalian Gene Collection (MGC)," Genome Research, 14(10B):2121-2127 (2004).
Gewurz, H., et al., "Structure and Function of the Pentraxins," Current Opinion in Immunology, 7(1):54-64 (1995).
Ghazizadeh, S., et al., "Physical and Functional Association of Src-Related Protein Tyrosine Kinases with FcγRII in Monocytic THP-1 Cells," Journal of Biological Chemistry, 269(12):8878-8884 (1994).
Giri, S., et al., "Antifibrotic Effect of Decorin in a Bleomycin Hamster Model of Lung Fibrosis," Biochemical Pharmacology, 54:1205-1216 (1997).
Gregory, S. G., et al., "The DNA Sequence and Biological Annotation of Human Chromosome 1", Nature 441(7091):315-321 (2006).
Hamazaki, Hideaki, "Structure and significance of N-linked sugar unit of human serum amyloid P component," Biochimica et Biochimica Acta, 1037(3):435-438 (1990).
Harris, J. M., et al., "Pegylation a Novel Process for Modifying Pharmacokinetics," Clin. Pharmacokinetics, 40(7):539-551 (2001).
Hartlapp, I., et al., "Fibrocytes Induce an Angiogenic Phenotype in Cultured Endothelial Cells and Promote Angiogenesis in Vivo," The FASEB Journal, 5(12):2215-2224 (2001).
Heegaard, N. H. H., et al., "Ligand-Binding Sites in Human Serum Amyloid P Component," Eur. J. Biochem. 239(3):850-856 (1996).
Hicks et al., "Serum amyloid P component binds to histones and activates the classical complement pathway", The Journal of Immunology, 149:3689-3694 (1992).
Hind, C. R. K., et al., "Human Serum Amyloid P Component, a Circulating Lectin with Specificity for the Cyclic 4,6-Pyruvate Acetal of Galactose: Interactions with Various Bacteria", Biochem. J., 225(1):107-111 (1985).
Hind, C. R., et al, "Binding specificity of serum amyloid P-component for the pyruvate acetal of galactose," Journal of Experimental Medicine, 159(4):1058-1069 (1984).
Hogaboam et al., "Chronic Airway Hyperreactivity,Goblet Cell Hyperplasia, and Peribronchial Fibrosis during Allergic Airway Disease Induced by Aspergillus fumigatus," American Journal of Phatology, vol. 156(2), pp. 723-732, (2000).
Hohenester, E., et al., "Crystal Structure of a Decameric Complex of Human Serum Amyloid P Component with Bound dAMP", J. Mol. Biol. 269(4):570-578 (1997).
Huang, Z. Y., et al., "The Monocyte Fcγ Receptors FcγRI/γ and FcγRIIA Differ in their Interaction with Syk and with Src-Related Tyrosine Kinases," J Leukoc Biol 76(2):491-499 (2004).
Hutchinson, W. L. , et al., "Human Serum Amyloid P Component is a Single Uncomplexed Pentamer in Whole Serum," Molecular Medicine, 6(6):482-493 (2000).
Ishaque, et al., "Role of Vitamins in Determining Apoptosis and Extent of Suppression by bel-2 During hybridoma Cell Culture," Apoptosis, 7(3):231-239 (2002).
Janeway, et al., Immunobiology, 3rd edition, Garland Publishing, pp. 3:1-3:11 (1997).
Jenny, N.S., et al., "Serum Amyloid P and Cardiovascular Disease in Older Men and Women Results from the Cardiovascular Health Study," Arterioscler. Thromb. Vasc. Biol., 27:352-358 (2007).
Junqueira, L. C.,et al., "Picrosirius Straining Plus Polarization Microscopy, A Specific Method for Collagen Detection in Tissue Sections," Histochem. J, 11(4):447-455 (1979).
Kiernan et al., "Proteomic characterization of novel serum amyloid P component variants from human plasm and urine," Proteomics, 4:1825-1829 (2004).
Kiernan, U.A., et al., "Selected Expression Profiling of Full-Length Proteins and Their Variants from Human Plasma," Clin. Proteomics 1:7-16 (2004).
Kinoshita CM, et al., "A Protease-Sensitive Site in the Proposed Ca2+-Binding Region of Human Serum Amyloid Component and Other Pentraxins." Protein Sci., 1:700-709 (1992).
Kisseleva, T., et al., "Bone Marrow-Derived Fibrocytes Participate in Pathogenesis of Liver Fibrosis," Journal of Hepatology, 45(3):429-438 (2006).
Kivela-Rajamaki, M. J., et al., "Laminin-5-γ2-chain and collagenase-2 (MMP-8) in Human Peri-Implant Sulcular Fluid," Clin. Oral Implants Res., 14(2):158-165 (2003).
Kolstoe et al., "Molecular dissection of Alzheimer's disease neuropathology by depletion of serum amyloid P component", PNAS, 106(18):7619-7623 (2009).
Korade-Mirnics, Z.,et al., "Src Kinase-Mediated Signaling in Leukocytes," J Leukoc Biol., 68(5):603-613 (2000).
Kucuk, H. F., et al., "Effect of a Selective Cyclooxygenase-2 Inhibitor on Renal Scarring," European Surgical Research, 38(5):451-457 (2006).
Lai, J. Y., et al., "Potent Small Molecule Inhibitors of Spleen Tyrosine Kinase (Syk)," Bioorganic & Medicinal Chemistry Letters, 13(18):3111-3114 (2003).
Lei, K. K., et al., "Genomic DNA Sequence for Human C-Reactive Protein," J. Biol. Chem. 260(24):13377-13383 (1985).
Lindenbaum, E. S., et al., "Serum-Free Cell Culture Medium Induces Acceleration of Wound Healing in Guinea-Pigs," Burns, 21(2):110-115 (1995).
Liu, T., et al., "Human Plasma N-Glycoproteome Analysis by Immunoaffinity Subtraction, Hydrazide Chemistry and Mass Spectrometry," J. Proteome Res., 4(6):2070-2080 (2005).
Majno, G., "Chronic Inflammation: Links With Angiogenesis and Wound Healing," American Journal of Pathology, 153(4):1035-1039 (1998).
Mantzouranis, E. C., et al., "Human Serum Amyloid P Component, cDNA Isolation, Complete Sequence of Pre-Serum Amyloid P Component, and Localization of the Gene to Chromosome 1," The Journal of Biological Chemistry, 260(12):7752-7756 (1985).
Marnell, L. L., et al., "C-Reactive Protein Binds to FcγRI in Transfected COS Cells," The Journal of Immunology, 155(4):2185-193 (1995).
Metz, C. N., "Fibrocytes: A Unique Cell Population Implicated in Wound Healing," Cell. Mol. Life Sci., 60(7):1342-1350 (2003).
Mold, C., et al., "Serum Amyloid P Component and C-Reactive Protein Mediate Phagocytosis Through Murine FcγRs," The Journal of Immunology, 166(2):1200-1205 (2001).

(56) References Cited

OTHER PUBLICATIONS

Moore, B. B., et al., "CCR2-Mediated Recruitment of Fibrocytes to the Alveolar Space After Fibrotic Injury," American Journal of Pathology, 166(3):675-684 (2005).
Mori, L., et al., "Fibrocytes Contribute to the Myofibroblast Population in Wounded Skin and Originate From the Bone Marrow," Exp Cell Res., 304(1):81-90 (2005).
Mortensen, R. F., et al., "Regulation of phagocytic leukocyte activities by C-reactive protein," Journal of Leukocyte Biology, 67(4):495-500 (2000).
Murphy, T. M., et al., "Extrahepatic Transcription of Human C-Reactive Protein," Journal of Experimental Medicine, 73(2):495-498 (1991).
Murray et al., "Serum amyloid P therapeutically attenuates murine bleomycin-induced pulmonary fibrosis via its effects on macrophages," PloS One, 5(3):e968 pp. 1-9 (2010).
Ohnishi, S. et al., "Isolation and Characterization of the Complete Complementary and Genomic DNA Sequences of Human Serum Amyloid P Component," J. Biochem, 100(4):849-858 (1986).
Oliveira, E. B., et al., "Primary Structure of Human C-Reactive Protein," The Journal of Biological Chemistry, 254(2):489-502 (1979).
Oriente, A., et al., "Interleukin-13 Modulates Collagen Homeostasis in Human Skin and Keloid Fibroblasts," The Journal of Pharmacology and Experimental Therapeutics, 292(3):988-994 (2000).
Osmand, A. P., et al., Partial Amino-Acid Sequences of Human and Rabbit C-Reactive Proteins: Homology with Immunoglobulins and Histocompatibility Antigens, Proc. Natl. Acad. Sci. U.S.A., 74(3):1214-1218 (1977).
Pachence, J., et al., "Tissue-Activated Delivery—Novel Methods for Site-Directed Drug Delivery," Drug Delivery Technology, 3(1):40-45 (2003).
Painter, R. H., "Evidence that C1t (Amyloid P-component) is not a subcomponent of the first component of complement (C1)," J. Immunol., 119(6):2203-2205 (1977).
Paul, William E., M.D., editor, Fundamental Immunology, 3d ed. Raven Press, p. 242 (1993).
Pepys et al., Glycobiology of Human Serum Amyloid P Component Amyloid Amyloidosis, *Proc. Int. Symp. Amyloidosis*, pp. 177-179 (1994).
Pepys, et al., "Targeted pharmacological depletion of serum amyloid P component for treatment of human amyloidosis", *Nature*, 471:254-259 (2002).
Pepys, et al., Human serum amyloid P component is an invariant constituent of amyloid deposits and has a uniquely homogeneous glycostructure, PNAS, 91:5206-5606 (1994).
Pepys, M. B., "Isolation of serum amyloid P-component (Protein SAP) in the Mouse," Immunology, 37(3):637-641 (1979).
Pepys, M. B., et al., "Amyloid P Component. A Critical Review," Amyloid: Int. J. Exp. Invest., 4(4):274-295 (1997).
Pepys, M. B., et al., "Serum Amyloid P Component is the Major Calcium-Dependent Specific DNA Binding Protein of Serum," Biochemical and Biophysical Research Communications, 148(1):308-313 (1987).
Pepys, MB, Serum Amyloid P. Component. Structure, Function and Role in Amlyoidosis. From Amlyoid & Amyloidosis 1998: Proceedings of the VIIIth International Symposium on Amyloidosis, Rochester, MN, pp. 6-10 (Aug. 7-11, 1998).
Philips, R. J., et al., "Circulating Fibrocytes Traffic to the Lungs in Response to CXCL 12 and Mediate Fibrosis," The Journal of Clinical Investigation, 114(3):438-446 (2004).
Pilling, D. et al., "Inhibition of Fibrocyte Differentiation by Serum Amyloid P," The Journal of Immunology, 17(10):5537-5546 (2003).
Pilling, D., et al., "Reduction of Bleomycin-Induced Pulmonary Fibrosis by Serum Amyloid P," The Journal of Immunology, 179(6):4035-4044 (2007).
Pontet, M., et al., "One step preparation of both human C-reactive protein and Cit," FEBS Letters, 88(2):172-175 (1978).

Portolano et al., "Lack of Promiscuity in Autoantigen-Specific H and L Chain Combinations as Revealed by Human H and L Chain "Roulette"," J. Immunol., 150(3):880-887 (1993).
Potempa, L. A., et al., "Effect of Divalent Metal Ions and pH Upon the Binding Reactivity of Human Serum Amyloid P Component, a C-Reactive Protein Homologue, for Zymosan," The Journal of Biological Chemistry, 260(22):12142-12147 (1985).
Prelli, F., et al., "The Primary Structure of Human Tissue Amyloid P Component From a Patient with Primary Idiopathic Amyloidosis," The Journal of Biological Chemistry, 260(24):12895-12898 (1985).
Quan et al., "The role of circulating fibrocytes in fibrosis" Current Rheumatology Reports. 8(2): 145-150 (2006).
Rudikoff et al., "Single amino acid substitution altering antigen-binding specificity," Proc Natl Acad Sci USA, 79(6):1979-1983 (1982).
Russo, et al., "Liver Fibrosis; Bone Marrow Functionality Contributes to Liver Fibrosis," 130(6) Gastroenterology Week Jul. 31, 2006 pp. 83-84 (2006).
Sada, K., et al., "Structure and Function of Syk Protein-Tyrosine Kinase," J Biochem, 130(2):177-186 (2001).
Saeland, E., at al., "Human C-reactive Protein Does not Bind to FcγRIIa on Phagocytic Cells," The Journal of Clinical Investigation, 107(5):641-643 (2001).
Sawada et al., "The Ace Inhibitor, Quinapril, Ameliorates Peritoneal Fibrosis in an Encapsulating Peritoneal Sclerosis Model in Mice" Pharmacological Research. 46(6): 505-510 (2002).
Schmidt, M., et al., "Identification of Circulating Fibrocytes as Precursors of Bronchial Myofibroblasts in Asthma," The Journal of Immunology, 171(1):380-389 (2003).
Schwalbe, et al., "Pentraxin Family of Proteins Interact Specifically with Phosphorylcholine and/or Phosporylethanolamine," Biochemistry, 31:4907-1645 (1992).
Shrive, A. K., et al., "Three Dimensional Structure of Human C-Reactive Protein," Nature Structural Biology, 3(4):346-354 (1996).
Siebert et al., "Effect of enzymatic desialylation of human serum amyloid P component on surface exposure of laser photo CIDNP (chemically induced dynamic nuclear polarization)—reactive histidine, tryptophan and tyrosine residues," *FEBS Letters*, 371(1):13-6 (1995).
Sjoblom, T., et al., "The Consensus Coding Sequences of Human Breast and Colorectal Cancers," Science, 314(5797):268-274 (2006).
Srinivasan, N., et al., "Comparative Analyses of Pentraxins: Implications for Protomer Assembly and Ligand Binding," Structure, 2(11):1017-1027 (1994).
Steel, D. M., et al., "The Major Acute Phase Reactants: C-Reactive Protein, Serum Amyloid P Component and Serum Amyloid A Protein," Immunology Today, 15(2):81-88 (1994).
Stein, M. P., et al., "C-reactive Protein Binding to FcγRIIa on Human Monocytes and Neutrophils is Allele-Specific," The Journal of Clinical Investigation, 105(3):369-376 (2000).
Su, L., et al., "Distinct Mechanisms of STAT Phosphorylation Via the Interferon-Alpha/Beta Receptor, Selective Inhibition of STAT3 and STAT5 by Piceatannol," Journal of Biological Chemistry 275(17):12661-12666 (2000).
Sutterwala, F. S., et al., "The Taming of IL-12 Suppressing the production of Proinflammatory Cytokines," Journal of Leukocyte Biology, 65(5):543-551 (1999).
Thompson, A. R., et al., "Human Plasma P Component: Isolation and Characterization," Biochemistry, 17(20):4304-4311 (1978).
Thompson, D., et al., "The Physiological Structure of Human C-Reactive Protein and its Complex with Phosphocholine", Structure, 7(2):169-177 (1999).
Tridandapani, S., et al., "Regulated Expression and Inhibitory Function of Fcγ-RIIb in Human Monocytic Cells," Journal of Biological Chemistry, The American Society for Biochemistry and Molecular Biology, Inc, 277(7):5082-5089 (2002).
Trinchieri, G., "Interleukin-12 and the Regulation of Innate Resistance and Adaptive Immunity," Nature Reviews Immunology, 3(2):133-146 (2003).
Tucci, A., et al., "Biosynthesis and Postsynthetic Processing of Human C-Reactive Protein," The Journal of Immunology, 131(5):2416-2419 (1983).

(56) References Cited

OTHER PUBLICATIONS

Turner, M., et al., "Tyrosine Kinase SYK: Essential Functions for Immunoreceptor Signalling," Immunology Today, 21(3):148-154 (2000).
Underwood, D. C., et al., "SB 239063, A p38 MAPK Inhibitor, reduces Neutrophilia, Inflammatory Cytokines, MMP-9, and Fibrosis in Lung," Am J Physiol Lung Cell Mol Physiol, 279:L895-L902 (2000).
Volanakis, J.E., "Human C-Reactive Protein: Expression, Structure, and Function," Molecular Immunology, 38(2-3):189-197 (2001).
Wang, Q., et al., "Effect of Antibody Against Integrin α4 on Bleomycin-Induced Pulmonary Fibrosis in Mice," Biochemical Pharmacology, 60:1949-1658 (2000).
Weimann, et al., "Studies of Wound Healing: Effects of Calcium D-Panthothenate on the Migration, Proliferation and Protein Synthesis of Human Dermal Fibroblasts in Culture," Interat. J. Vit. Nutr. Res., 69(2):113-119 (1999).
Whitehead, A. S., et al., "Isolation of Human C-Reactive Protein Complementary DNA and Localization of the Gene to Chromosome 1," Science, 221(4605):69-71 (1983).
Woo, P., et al., "Characterization of Genomic and Complementary DNA Sequence of Human C-Reactive Protein, and Comparison with the Complementary DNA Sequence of Serum Amyloid P Component," The Journal of Biological Chemistry, 260(24):13384-13388 (1985).
Wynn, T. A., "IL-13 Effector Functions," Annu Rev Immunol., 2:425-456 (2003).
Yang, L., et al., "Identification of Fibrocytes in Postburn Hypertrophic Scar," Wound Repair and Regeneration, 13(4):398-404 (2005).
Yang, L., et al., "Peripheral Blood Fibrocytes From Burn Patients: Identification and Quantification of Fibrocytes in Adherent Cells Cultured From Peripheral Blood Mononuclear Cells," Laboratory Investigation, 82(9):1183-1192 (2002).
Yu, L., et al., "Therapeutic Strategies to Halt Renal Fibrosis," Current Opinion in Pharmacology, 2:177-181 (2002).
Zahedi K., "Characterization of the Binding of Serum Amyloid P To Type IV Collagen," The Journal of Biological Chemistry, 271(25):14897-14902 (1996).
Zahedi, K., "Characterization of the Binding of Serum Amyloid P to Laminin," The Journal of Biological Chemistry, 272(4):2143-2148 (1997).
Zhang, R., et al., "C-reactive Protein Impairs Human CD14(+) Monocyte-Derived Dendritic Cell Differentiation, Maturation and Function," European Journal of Immunology, 36(11):2993-3006 (2006).
Boysen, S. et al., "Recombinant human serum amyloid P component from Pichia pastoris: production and characterization," Protein Expression and Purification, vol. 35(2): 284-292 (2004).
Heegaard, N.H.H., "Microscale characterization of the structure-activity relationship of a heparin-binding glycopeptide using affinity capillary electrophoresis and immobilized enzymes," Journal of Chromatography, vol. 853(1-2):189-195 (1999).
Ilium, Lisbeth, "Nasal Drug Delivery-possibilities, problems and solutions," Journal of Controlled Release, vol. 87(1-3):187-198 (2003).
Kawashima et al., Pulmonary delivery of insulin with nebulized DL-lactide/glycolide copolymer (PLGA) nanospheres to prolong hypoglycemic effect, Journal of Controlled Release, vol. 62(1-2): 279-287 (1999).
Moreira et al., "Serum amyloid P attenuates M2 macrophage activation and protects against fungal spore-induced allergic airway disease," Journal of Allergy and Clinical Immunology, vol. 126(4), pp. 712-721 (2010).
Siebert, Hans-Christian et al., "Comparison between intact and desialylated human serum amyloid P component by laser photo CIDNP (chemically induced dynamic nuclear polarization) technique: An indication for a conformational impact of sialic acid," Glycoconjugate Journal, vol. 14(8):945-949 (1997).

Tennent et al., "Macrophage dependent elimination of amyloid following treatment with anti-SAP antibody," Amyloid: The International Journal of Experimental and Clinical Investigation, vol. 17(1); p. 51 (2010).
Azuma et al., "Superagonistic CD28 antibody induces donor-specific tolerance in rat renal allografts", American Journal of Transplantation, 8:2004-2014 (2008).
Bharadwaj et al., "Serum amyloid P component binds to Fc gamma receptors and opsonizes particles for phagocytosis," The Journal of Immunology, 166:6735-6741 (2001).
Biro et al., "Activated complement components and complement activator molecules on the surface of cell-derived microparticles in patients with rheumatoid arthritis and healthy individuals," Annals of the Rheumatic Diseases, 66(:1085-1092 (2007).
Giorgini et al., "Blockade of chronic graft-versus-host disease by alloantigen-induced CD4+CD25+Foxp3+ regulatory T cells in nonlymphopenic hosts," Journal of Leukocyte Biology, 82:1053-1061 (2007).
Guyre et al., "Receptor modulation by Fc gamma RI-specific fusion proteins is dependent on receptor number and modified by IgG," The Journal of Immunology, 167:6303-6311 (2001).
Hundt et al., "Treatment of acute exacerbation of systemic lupus erythematosus with high-dose intravenous immunoglobulin," Rheumatology, 39:1301-1302 (2007).
Kessel et al., "Intravenous immunoglobulin therapy affects T regulatory cells by increasing their suppressive function," The Journal of Immunology, 179:5571-5575 (2007).
Lu et al., "Structural recognition and functional activation of FcγR by innate pentraxins," Nature 456(7224):989-992 (2008).
Pilling et al., "Aggregated IgG inhibits the differentiation of human fibrocytes," Journal of Leukocyte Biology, 79:1242-1251 (2006).
Shoenfeld et al., "The mosaic of autoimmunity: prediction, autoantibodies, and therapy in autoimmune diseases—2008", Israel Medical Association Journal, 10:13-19 (2008).
Thomson et al., "Lentivirally transduced recipient-derived dendritic cells serve to ex vivo expand functional FcRgamma-sufficient double-negative regulatory T cells," Molecular Therapy, 15(4):818-824 (2007).
Toubi et al., High-dose intravenous immunoglobulins: an option in the treatment of systemic lupus erythematosus, Human Immunology, 66(4):395-402 (2005).
International Search Report, PCTUS/2010/026841 dated Jul. 9, 2010.
Garcia de Frutos et al., "Serum Amyloid P Component Binding to C4b-binding Protein," The Journal of Biological Chemistry: 270(45):26950-26955 (1995).
Rudinger, J., "Characteristics of the amino acids as components of a peptide hormone sequence," Peptide Hormones:1-7 (1975).
<http://en.wikipedia.org/wiki/Pentraxins> downloaded from the internet on Apr. 16, 2013.
<http://en.wikipedia.org/wiki/Serum_amyloid_P_component> downloaded from the internet on Apr. 16, 2013.
Banham et al., "FOXP3+ regulatory T cells: Current controversies and future perspectives," European Journal of Immunolgoy, vol. 36(11): 2832-2836 (2006).
Tanaka and Sakaguchi, "Regulatory T cell and autoimmune diseases," Japanese Journal of Clinical Immunology, vol. 28(5): 291-299 (2005), English Abstract only.
Zheng, J., et al., "Piceatannol, a Stilbene Phytochemical, Inhibits Mitochondrial FOF1-ATPase Activity by Targeting the FI Complex," Biochemical and Biophysical Research Communications, 261(2):499-503 (1999).
Li et al., "Human amyloid P component: a Circulating lectin that modulates immunological response," Scand. J. Immun. 19(3):227-236 (1984).
Murray et al., "TGF-beta driven lung fibrosis is macrophage dependent and blocked by Serum amyloid P," The International Journal of Biochemistry & Cell Biology, vol. 43: 154-162 (2011).
Hori, Shohel "Control of autoimmunity by Foxp3+ Treg cells" Journal of Clinical and Experimental Medicine, vol. 227(5), 294-298 (2008) (English abstract).

(56) References Cited

OTHER PUBLICATIONS

Chu et al., "Murine models of chronic graft-versus-host disease: insights and unresolved issues," Biology of Blood and Marrow Transplantation, 14(4):365-378 (2008).

Morel, "Mouse Models of Human Autoimmune Diseases: Essential Tools That Require the Proper Controls," PloS Biol, 2(8):e224-e241 (2004).

Edinger, et al., "$CD4^+CD25^+$ Regulatory T Cells Preserve Graft-Versus-Tumor Activity While Inhibiting Graft-Versus-Host Disease After Bone Marrow Transplantation," *Nature Medicine*, 9(9):1144-1150 (Sep. 2003).

Ji, et al., "SAP Suppresses the Development of Experimental Autoimmune Encephalomyelitis in C57BL/6 Mice," *Immunology and Cell Biology*, pp. 1-8, (2011).

Luth, et al., "Ectopic Expression of Neural Autoantigen in Mouse Liver Suppresses Experimental Autoimmune Neuroinflammation by Inducing Antigen-Specific Tregs," *The Journal of Clinical Investigation*, 118(10);3403-3410, (Oct. 2008).

* cited by examiner

Figure 1

```
Homo sapiens     H T D L S G K V F V F P R E S V T D H V N L I T P L E K P L
Gallus gallus    Q E D L Y R K V F V F R E D P S D A Y V L L Q V Q L E R P L
Bos taurus       Q T D L R G K V F V F P R E S S T D H V T L I T K L E K P L
C. migratorius   Q T D L T G K V F V F P R E S E S D Y V K L I P R L E K P L Homo sapiens     Q N F T L C F R A Y S D L S R A Y S L F S Y N T Q G R D N E
Gallus gallus    L N F T V C L R S Y T D L T R P H S L F S Y A T K A Q D N E
Bos taurus       K N L T L C L R A Y S D L S R G Y S L F S Y N I H S K D N E
C. migratorius   E N F T L C F R T Y T D L S R P H S L F S Y N T K N K D N E Homo sapiens     L L V Y K E R V G E Y S L Y I G R H K V T S K V I E K F P A
Gallus gallus    I L L F K P K P G E Y R F Y V G G K Y V T F R V P E N R G E
Bos taurus       L L V F K N G I G E Y S L Y I G K T K V T V R A T E K F P S
C. migratorius   L L I Y K E R M G E Y G L Y I E N V G A I V R G V E E F A S Homo sapiens     P V H I C V S W E S S S G I A E F W I N G T P L V K K G L R
Gallus gallus    W E H V C A S W E S G S G I A E F W L N G R P W P R K G L Q
Bos taurus       P V H I C T S W E S S T G I A E F W I N G K P L V K R G L K
C. migratorius   P V H F C T S W E S S S G I A D F W V N G I P W V K K G L K Homo sapiens     Q G Y F V E A Q P K I V L G Q E Q D S Y G G K F D R S Q S F
Gallus gallus    K G Y E V G N E A V V M L G Q E Q D A Y G G G F D V Y N S F
Bos taurus       Q G Y A V G A H P K I V L G Q E Q D S Y G G G F D K N Q S F
C. migratorius   K G Y T V K T Q P S I I L G Q E Q D N Y G G G F D K S Q S F Homo sapiens     V G E I G D L Y M W D S V L P P E N I L S A Y Q G T P L P A
Gallus gallus    T G E M A D V H L W D A G L S P D K M R S A Y L A L R L P P
Bos taurus       M G E I G D L Y M W D S V L S P E E I L L V Y Q G S S S I S
C. migratorius   V G E M G D L N M W D S V L T P E E I K S V Y E G S W L E P Homo sapiens     N I L D W Q A L N Y E I R G Y V I I K P L V W V
Gallus gallus    A P L A W G R L R Y E A K G D V V V K P R L R E A L G A
Bos taurus       P T I L D W Q A L K Y E I K G Y V I V K P M V W G
C. migratorius   N I L D W R A L N Y E M S G Y A V I R P R V W H
```

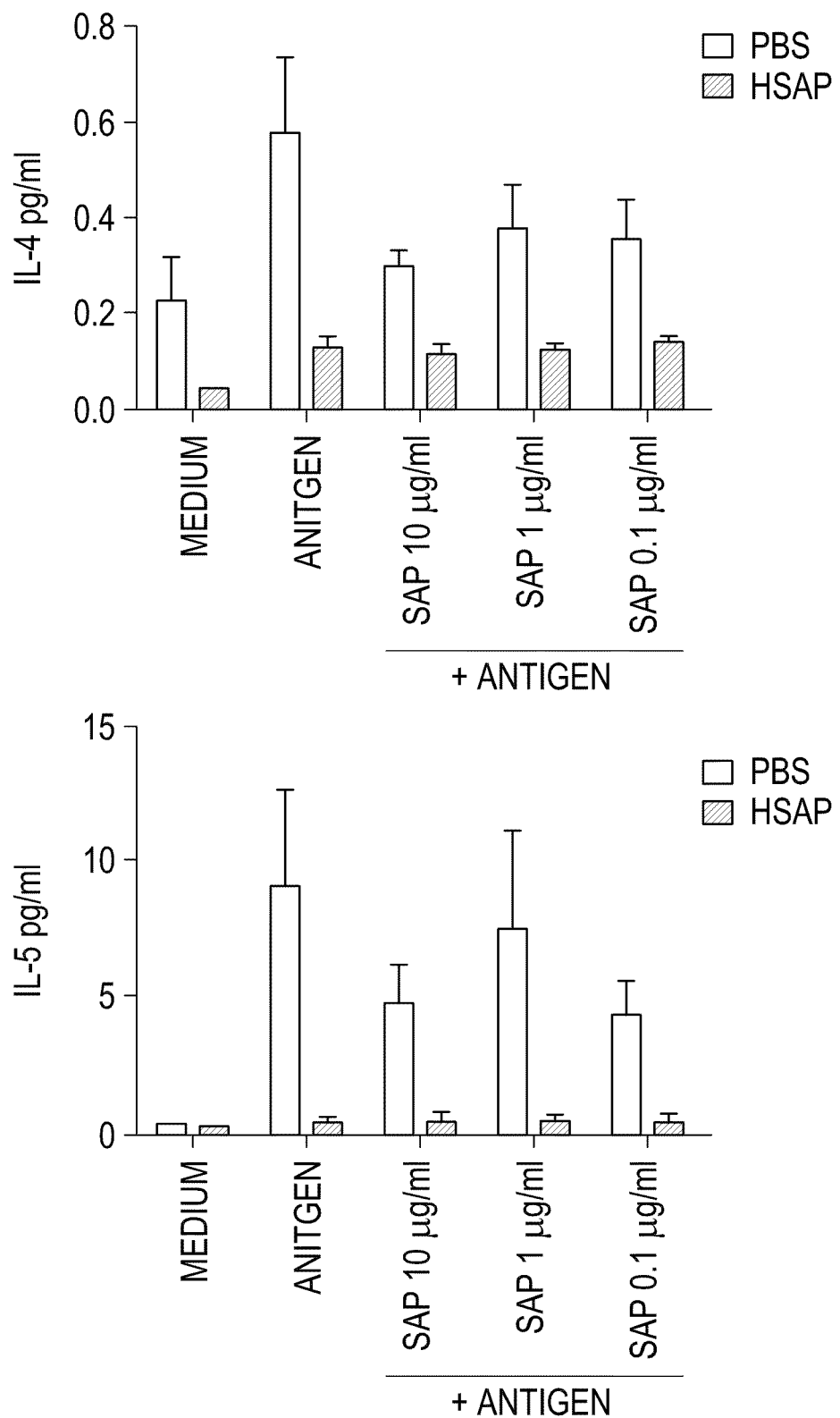
Figure 3A (part 1)

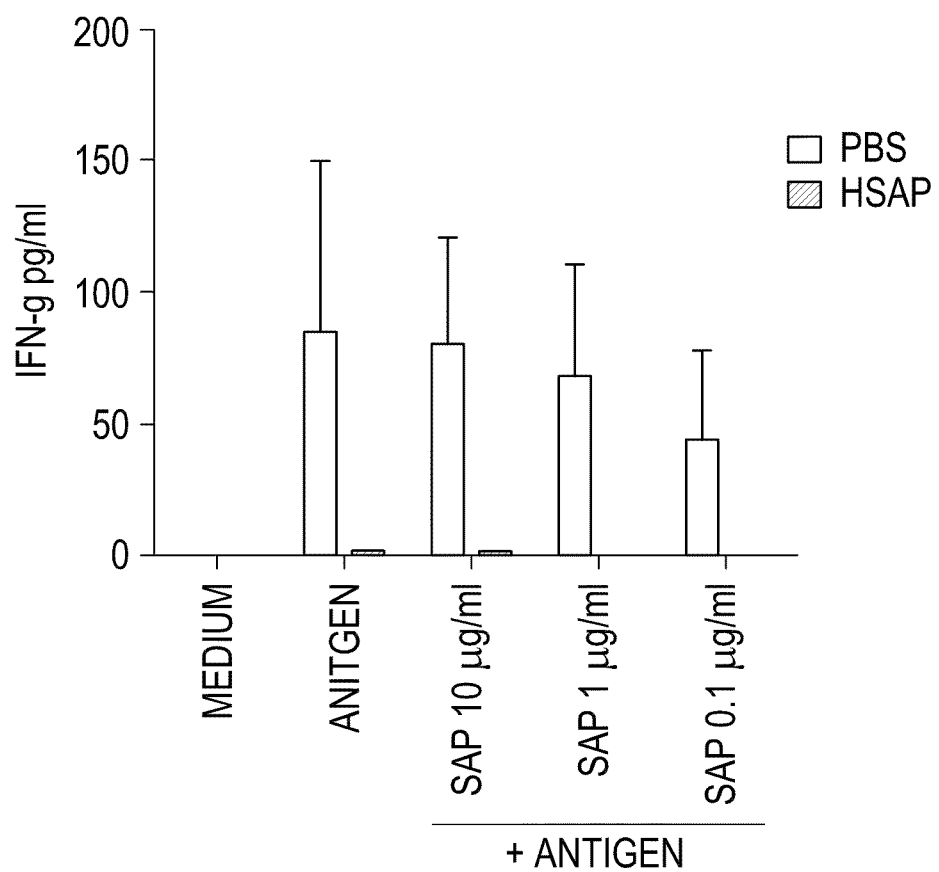
Figure 3A (part 2)

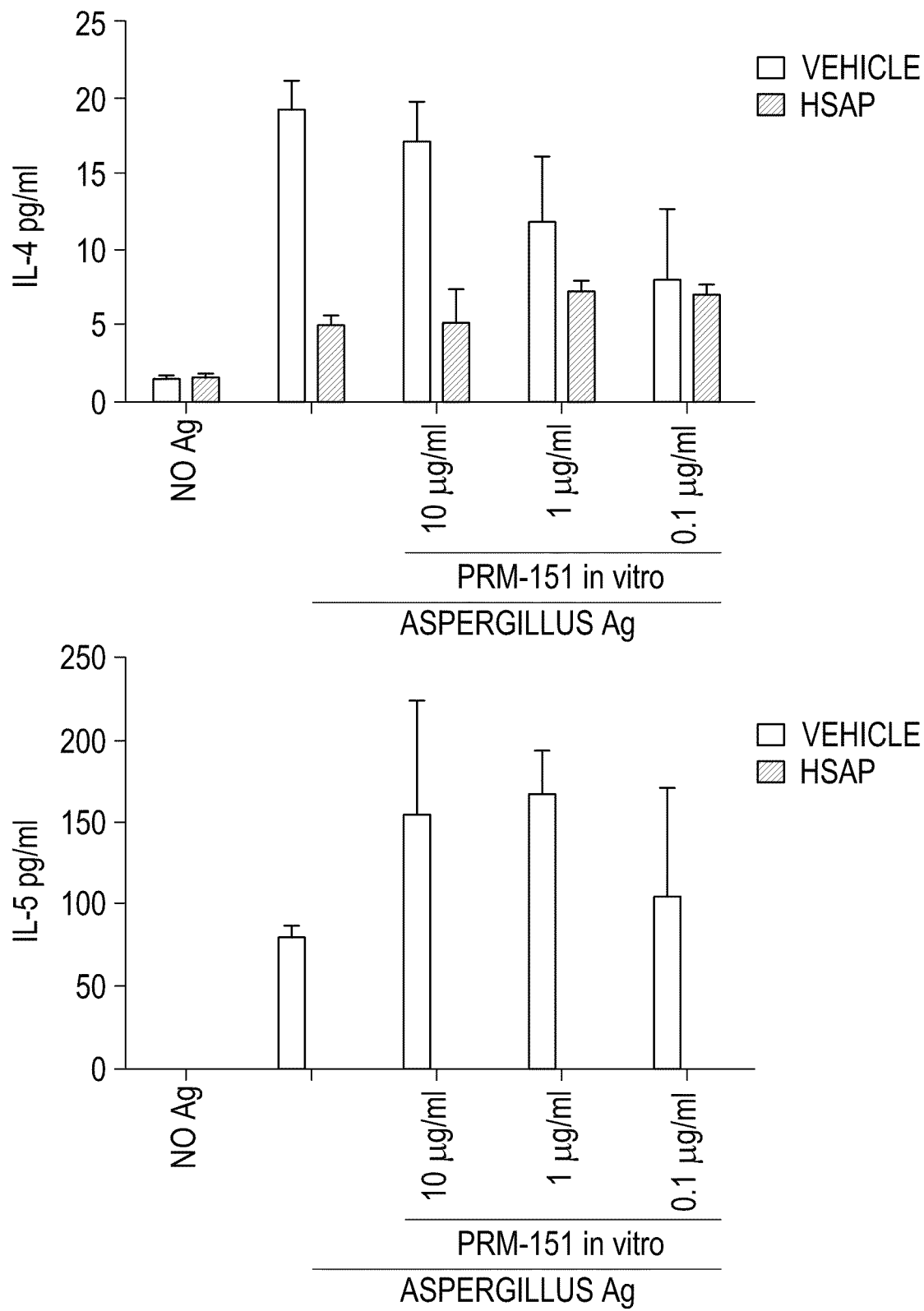
Figure 3B (part 1)

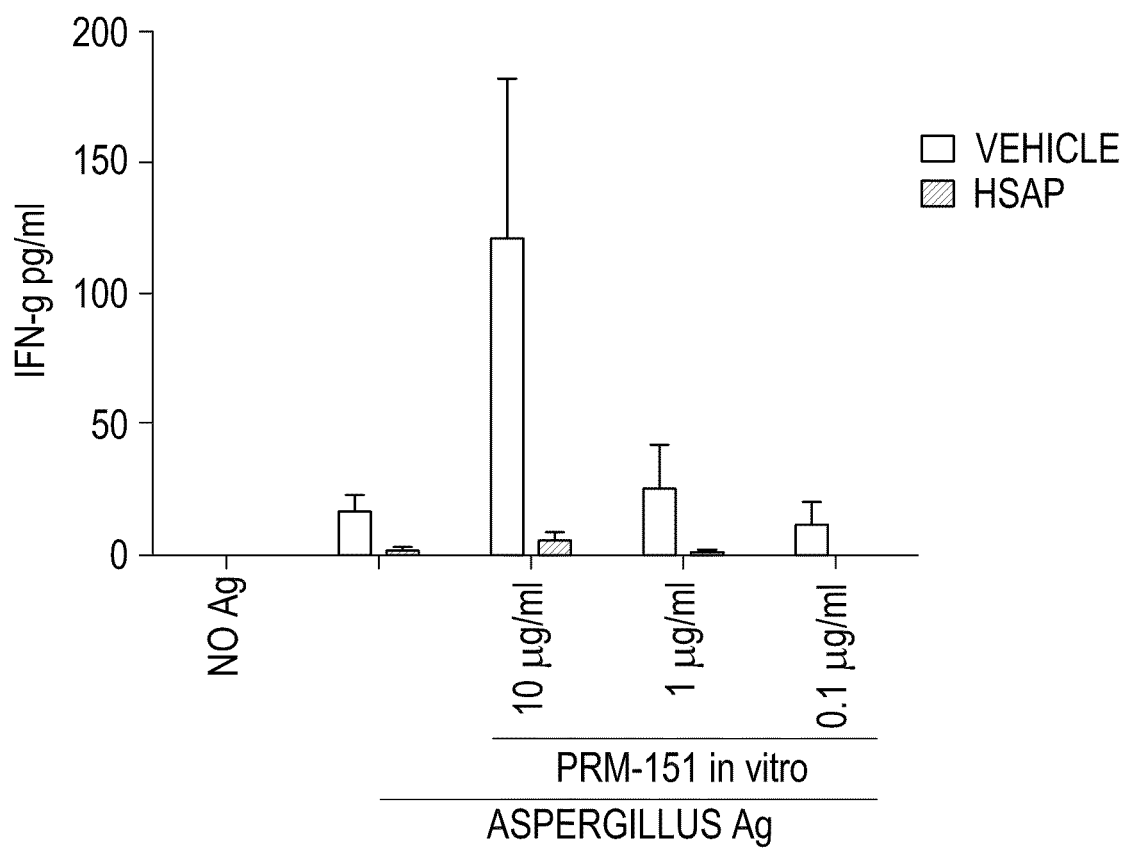
Figure 3B (part 2)

TREATMENT METHODS FOR AUTOIMMUNE DISORDERS

CROSS-REFERENCE TO RELATED APPLICATIONS

This application claims the benefit of U.S. Provisional Application Ser. No. 61/209,845 filed Mar. 11, 2009. All the teachings of the above-referenced application is incorporated herein by reference.

SEQUENCE LISTING

The instant application contains a Sequence Listing which has been submitted via EFS-Web and is hereby incorporated by reference in its entirety. Said ASCII copy, created on Apr. 30, 2010, is named 10411214.txt and is 7,519 bytes in size.

BACKGROUND OF THE INVENTION

Immune tolerance is central to the immune system's ability to differentiate between self and foreign proteins. Central tolerance is initially achieved during thymic selection by the deletion of self-reactive T cells. However, central tolerance is incomplete, and further immune regulation is required in the periphery. Peripheral mechanisms of T cell regulation include the induction of anergy, activation induced cell death, and modulation of T cell activity.

Regulatory T cells are fundamental in controlling various immune responses. Absence or defective function of regulatory T cells has been correlated with autoimmunity in humans, whereas their presence has been associated with tolerance. Compelling data from preclinical animal models indicates that adoptive transfer of regulatory T cells can prevent or cure several T cell-mediated diseases, including autoimmune diseases and allograft rejection by restoring immune tolerance to self antigens or alloantigens. Three categories of regulatory T cells have been described within the CD4+ T lymphocyte cell population: TH3 cells, Type 1 regulatory cells, and CD4+CD25+ T regulatory cells. TH3 cells function via the secretion of TGF-β and can be generated in vitro by stimulation in the presence of IL-4 or in vivo through oral administration of low dose antigens (Chen et al., Science 265:1237-1240, 1994; Inobe et al., Eur. J. Immunol. 28:2780-2790, 1998). Type 1 regulatory T cells suppress T cells through the production of IL-10 and TGF-β and are derived by stimulation of memory T cells in the presence of IL-10 (Groux et al., Nature 389:737-742, 1996; Groux et al., J. Exp. Med. 184:19-29, 1996). CD4+CD25+ regulatory T cells are thought to function as a regulator of autoimmunity by suppressing the proliferation and/or cytokine production of CD4+CD25− T cell responder cells at the site of inflammation. Furthermore, these T regulatory cells decrease the magnitude of the immune response, allowing innocuous antigen to be removed without inducing pathology.

CD4+CD25+ regulatory T cells are present in both humans and mice and are characterized by expression of CD25 (for review, see Sakaguchi et al., Immunol. Rev. 182:18-32). Regulatory T cells isolated from human peripheral blood are highly differentiated memory cells based on their FACS staining characteristics and short telomere length and historically are thought to be derived from the thymus (Taams et al., Eur. J. Immunol. 32:1621-1630, 2002; Jonuleit et al., J. Exp. Med. 193:1285-1294, 2001). In humans, regulatory T cells are believed to represent 1-3% of all CD4+ T cells and require activation to induce suppressor function. The suppressive function of these regulatory T cells is mainly mediated via cell-cell contact and is abrogated by the addition of IL-2 (Baecher-Allan et al., J. Immunol 167:1245-1253, 2001).

The regulatory T cell population is reduced in autoimmune-prone animals and humans (see Salomon et al., Immunity 12:431-440, 2000; Kukreja et al., J. Clin. Invest. 109: 131-140, 2002). Mice carrying the X-linked scurfy mutation develop a multi-organ autoimmune disease and lack conventional CD4+CD25+ regulatory T cells (Fontenot et al., Nat. Immunol. 4:330-336, 2003; Khattri et al., Nat. Immunol. 4:337-342, 2003). It has been shown that the gene mutated in these mice is FoxP3, which encodes a member of the forkhead/winged helix family and acts as a transcriptional repressor (Schubert et al., J. Biol. Chem. 276:37672-37679, 2001). In mice, FoxP3 has been shown to be expressed exclusively in CD4+CD25+ regulatory T cells and is not induced upon activation of CD25− cells. However, when FoxP3 is introduced via retrovirus or via transgene expression, naive CD4+CD25− T cells are converted to regulatory T cells (Hori et al., Science 299:1057-1061, 2003). In humans, it has been noted that mutations in FoxP3 lead to a severe lymphoproliferative disorder known as IPEX (immunodysregulation, polyendocrinopathy, enteropathy, X-linked) syndrome, characterized by lymphoproliferative disease, insulin-dependent diabetes, thyroiditis, eczema and death at an early age (see Wildin et al., J. Med. Genet. 39:537-545, 2002).

The CD4+CD25+ regulatory population is heterogeneous, as 20-30% also express HLA-DR. The DR+ regulatory T cells inhibit T-cell proliferation and cytokine production via an early contact-dependent mechanism that is associated with an additional induction of FoxP3 mRNA. In contrast, DR− regulatory T cells do not induce early contact-dependant suppression but rather initially enhance secretion of IL-10 and IL-4. Eventually, DR− regulatory T cells induce a late suppression of proliferation that is associated with a delayed increase in FoxP3 mRNA by the regulatory T cells. Thus, both DR+ and DR− regulatory T cells can suppress via a cell-contact-mediated mechanism, but the DR− population can also suppress by inducing the secretion of IL-10. Therefore, it is possible that different types of autoimmune diseases may be associated with a defect in suppression by either DR+ or DR− regulatory T cells.

Due to their low frequency in peripheral blood, freshly isolated human CD4+CD25+ T cells with suppressive function are difficult to isolate and expand. In the autoimmune NOD mouse model, one group of investigators has recently isolated naturally occurring antigen-specific regulatory T cells from mouse spleen and lymph nodes. These regulatory T cells were expanded ex vivo and transferred to the diabetic prone NOD mouse. Transplantation of these regulatory T cells was demonstrated to suppress the development of diabetes (Tang et al., J. Exp. Med. 199:1455-1465, 2004, Masteller et al., J. Immunol 175:3053-3059, 2005; Tarbell et al., J. Exp Med 199:1467-1477, 2004). This approach demonstrates the therapeutic benefit of regulatory T cell transfer to treat autoimmune disease. However, the approach used in the NOD mouse model is not therapeutically applicable to human subjects, due to the requirement that a large number of rare CD4+CD25+ T cells (approximately 4% of circulating T cells) need to be isolated from the peripheral blood. Further, this mouse model contains a single fixed T cell receptor (TCR) and does not address the problem of following TCR repertoire evolution or identifying antigen-specific T cells in complex systems where a polyclonal T cell response is present. Similar studies have not been possible in human subjects due to the low frequency of antigen-specific regulatory T cells circulating in the peripheral blood, especially with respect to autoreactive T cells.

Type I regulatory cells arise in the periphery after encounter with antigen in the presence of IL-10. The unique cytokine production profile (IL-$2^{low/-}$ IL-$4^-$, IL-$5^+$, IL-$10^+$, TGF-$\beta^+$) distinguishes Type I regulatory cells from T helper 0 ($T_0$1) and $T_H$2 cells. To date, no specific cell-surface markers for Type I regulatory cells have been identified. Type I regulatory cells have a very low proliferative capacity following activation in vitro through the T cell receptor, in part due to autocrine production of IL-10. Type I regulatory cells regulate immune responses through the secretion of the immunosuppressive cytokines IL-10 and TGF-$\beta$, and they suppress both naïve and memory T cell responses and downregulate the expression of co-stimulatory molecules and pro-inflammatory cytokines by antigen-presenting cells. Furthermore, Type I regulatory cells favor the production of IgD, IgA, and IgG by B cells. Importantly, Type I regulatory cells are inducible, antigen-specific, and need to be activated through their TCR to exert their suppressive functions. However, once activated, they mediate suppression in an antigen non-specific manner (Roncarolo et al. *Immunol. Rev.* 2006. 212: 28-50).

Given the important role regulatory T cells play in immune tolerance, there is a need to develop methods for generating, selecting and expanding human regulatory T cells for use in the treatment and/or prevention of autoimmune diseases, inflammatory conditions, and for the prevention of graft rejection in a recipient following solid organ or stem cell transplantation.

SUMMARY OF THE INVENTION

In part, the disclosure demonstrates that serum amyloid P (SAP) and SAP agonists are useful in the treatment of autoimmune disorders. One aspect of the disclosure provides methods for treating or preventing an autoimmune disorder or condition in a patient in need thereof by administering a therapeutically effective amount of an SAP agonist. The SAP agonist may promote regulatory T cell-mediated suppression of the autoimmune disorder or condition. The administration of an SAP agonist may inhibit the onset of an autoimmune disorder or condition, reduce the number of days a patient is afflicted with an autoimmune disorder or condition, and/or reduce the severity of a hypersensitivity disorder or condition. The disclosure provides methods for treating both patients afflicted with an autoimmune disorder, as well as patients at risk of developing an autoimmune disorder. In some embodiments, the administration of an SAP agonist may commence prior to, concurrently with, or after treatments or other events that may place patients at risk for developing an autoimmune disorder. In certain aspects, SAP agonists are useful in treating an autoimmune disorder before the onset of fibrosis. In some embodiments, the patient is administered an additional active agent. In certain aspects, the additional active agent is a therapeutic agent used to treat or prevent the autoimmune disorder or symptoms. In certain embodiments, SAP and SAP agonists are useful in treating autoimmune disorders or conditions before the onset of fibrosis.

The disclosure further provides methods for treating or preventing graft-versus-host disease in a patient in need thereof by administering a therapeutically effective amount of an SAP agonist. The SAP agonist may promote regulatory T cell-mediated suppression of the graft-versus-host disease. The administration of an SAP agonist may inhibit the onset of an autoimmune disorder or condition, reduce the number of days a patient is afflicted with an autoimmune disorder or condition, and/or reduce the severity of the graft-versus-host disease. The disclosure provides methods for treating both patients afflicted with graft-versus-host disease, as well as patients at risk of developing graft-versus-host disease. In some embodiments, the administration of an SAP agonist may commence prior to, concurrently with, or after treatments that may place patients at risk for developing graft-versus-host disease. In certain aspects, SAP agonists are useful in treating graft-versus-host disease before the onset of fibrosis. In some embodiments, the patient is administered an additional active agent. In certain aspects, the additional active agent is a therapeutic agent used to treat or prevent graft-versus-host disease. In certain embodiments, SAP and SAP agonists are useful in treating graft-versus-host disease before the onset of fibrosis.

The disclosure further comprises methods for treating or preventing an autoimmune disorder or condition in a patient using regulatory T cells. The method comprises obtaining a sample containing T cells, contacting the T cell sample with an SAP agonist in an ex vivo culture to produce a population of cells enriched for regulatory T cells, isolating the regulatory T cells, and administering a therapeutically effective amount of the isolated regulatory T cells to the patient to treat or prevent an autoimmune disorder or condition. In some embodiments, the regulatory T cells are FoxP$3^+$ and/or IL-10 producing regulatory T cells. The SAP agonist may promote regulatory T cell-mediated suppression of the autoimmune disorder or condition. The administration of regulatory T cells may inhibit the onset of an autoimmune disorder or condition, reduce the number of days a patient is afflicted with an autoimmune disorder or condition, and/or reduce the severity of an autoimmune disorder or condition. The disclosure provides methods for treating both patients afflicted with an autoimmune disorder, as well as patients at risk of developing an autoimmune disorder. In some embodiments, the administration of regulatory T cells may commence prior to, concurrently with, or after treatments that may place patients at risk for developing an autoimmune disorder. In some embodiments, the regulatory T cells are administered on a periodic basis. In certain aspects, regulatory T cells are useful in treating an autoimmune disorder before the onset of fibrosis. In some embodiments, the patient is administered at least one additional active agent. In certain aspects, the additional active agent is a therapeutic agent used to treat or prevent the autoimmune disorder. In certain aspects, the additional active agent is an SAP agonist. In certain aspects, the additional active agent is a cytokine. Cytokines useful in the methods of the present invention include, but are not limited to, IL-2, IL-4, IL-10, TGF-$\beta$, IL-15 and/or IL-17. In some embodiments, the additional active agent is administered on a periodic basis.

The disclosure additionally provides methods for treating or preventing an adverse immune response in a patient that has undergone, or will undergo, an organ or tissue transplant. The method comprises obtaining a sample containing a T cell, contacting the T cell sample with an SAP agonist in an ex vivo culture to produce a population of cells enriched for regulatory T cells, isolating the regulatory T cells, and administering a therapeutically effective amount of the isolated regulatory T cells to the patient to treat or prevent an adverse immune response. In certain embodiments, the patient is administered an SAP agonist prior to obtaining the T cell containing sample. In some embodiments, the regulatory T cells are FoxP$3^+$ and/or IL-10 producing regulatory T cells. In some embodiments, the transplant organ or tissue is a solid organ selected from kidney, heart, lung, liver, pancreas or corneal tissue. In some embodiments, the transplant organ or tissue is blood or bone marrow. In certain aspects, the adverse immune response is graft-versus-host disease. In certain aspects, the regulatory T cells are administered at least one day before transplantation. In certain aspects, the regulatory T cells are administered from one to five days after transplantation. In certain aspects, the regulatory T cells are administered on a periodic basis. In some embodiments, the patient is administered at least one additional active agent. In certain aspects, the additional active agent is a therapeutic agent used to treat or prevent graft-versus-host disease. In some embodiments, the additional active agent is an SAP agonist. In certain aspects, the additional active agent is a cytokine. Cytokines useful by the methods of the present invention include, but are not limited to, IL-2, IL-4, IL-10, TGF-β, IL-15 and/or IL-17. In some embodiments, the additional active agent is administered on a periodic basis. In certain embodiments, regulatory T cells of the invention are useful in treating or preventing an adverse immune response in a patient that has undergone, or will undergo, an organ or tissue transplant before the onset of fibrosis.

The disclosure further provides a composition comprising a population of isolated FoxP3$^+$ regulatory T cells and a pharmaceutically acceptable carrier that is suitable for use in a human patient. In some embodiments, the composition further comprises at least one additional active agent. In certain embodiments, the additional active agent is an SAP agonist. In certain aspects, the additional active agent is a cytokine. Cytokines useful in the methods of the present invention include, but are not limited to, IL-2, IL-4, IL-10, TGF-β, IL-15 and/or IL-17. In certain embodiments, the additional active agent is a therapeutic agent used to treat or prevent the autoimmune disorder.

The disclosure provides methods for producing a population of cells enriched for regulatory T cells by providing a peripheral blood mononuclear cell sample (PBMC), contacting the PBMC sample with an SAP agonist, and co-culturing the PBMC sample with T cells. In some embodiments, the PBMC sample comprises T cells. In certain aspects, the regulatory T cells are FoxP3$^+$ and/or IL-10 producing regulatory T cells.

The disclosure further provides methods for treating an autoimmune disorder in a patient by providing peripheral blood mononuclear cell (PBMC) sample, contacting the PBMC sample with an SAP agonist while co-culturing with T cells to produce a population of cells enriched for regulatory T cells, and administering the regulatory T cells into the patient.

The disclosure additionally provides methods for producing a population of cells enriched for regulatory T cells by providing a population of T cells and contacting the T cells with an SAP agonist.

The disclosure further provides methods for expanding regulatory T cells by contacting a population of regulatory T cells with an SAP agonist. In some embodiments, the contacting is effected ex vivo. In some embodiments, the contacting is effected in vivo by administering the SAP agonist to a patient. In certain aspects, the patient is afflicted with or at risk for developing an autoimmune disease. In certain aspects, the patient is afflicted with graft-versus-host disease. In certain aspects, the population of regulatory T cells includes FoxP3$^+$ and/or IL-10 producing regulatory T cells.

Autoimmune disorders or conditions that can be treated by the methods of the disclosure include, but are not limited to, type I diabetes, multiple sclerosis, rheumatoid arthritis, psoriatic arthritis, autoimmune myocarditis, pemphigus, myasthenia gravis, Hashimoto's thyroiditis, Graves' disease, Addison's disease, autoimmune hepatitis, chronic Lyme arthritis, familial dilated cardiomyopathy, juvenile dermatomyositis, polychondritis, Sjogren's syndrome, psoriasis, juvenile idiopathic arthritis, inflammatory bowel disease, systemic lupus erythematosus, and graft-versus-host disease. In certain embodiments, SAP agonists and regulatory T cells of the invention are useful in treating autoimmune disorders or conditions before the onset of fibrosis. In certain embodiments, SAP agonists and regulatory T cells of the invention are useful in treating rheumatoid arthritis before the onset of fibrosis. In certain embodiments, SAP agonists and regulatory T cells of the invention are useful in treating psoriatic arthritis before the onset of fibrosis. In certain embodiments, SAP agonists and regulatory T cells of the invention are useful in treating psoriasis before the onset of fibrosis. In certain embodiments, SAP agonists and regulatory T cells of the invention are useful in treating systemic lupus erythematosus before the onset of fibrosis. In certain embodiments, SAP agonists and regulatory T cells of the invention are useful in treating inflammatory bowel disease before the onset of fibrosis.

In certain aspects, SAP agonists and regulatory T cells of the disclosure maybe used to treat, prevent, or reduce the severity of an inflammatory eye disease including, for example, dry eye diseases, allergic conjunctivitis, uveitis, and uveoretinitis as well as eye inflammation associated with corneal transplant, neoplastic disorders, and congenital disorders.

The disclosure provides SAP agonists useful in the methods of the disclosure. SAP agonists may be administered topically, by injection (e.g., intravenous injection), by inhalation, continuous depot or pump, or any combination thereof. SAP agonists may increase or mimic SAP signaling, increase SAP activity, increase SAP mRNA and/or protein expression, or increase SAP levels in serum. An SAP agonist may be a small molecule, nucleic acid, polypeptide, or antibody. In certain aspects, the SAP agonist is an SAP polypeptide, an anti-FcγRI antibody, an anti-FcγRII antibody, an anti-FcγRIII antibody, a cross-linked anti-FcγR antibody, an aggregated IgG antibody, or a cross-linked IgG antibody. The SAP agonist may be formulated to be administered conjointly with one or more SAP agonists or other active agents.

Additional active agents that may be conjointly administered with SAP agonists include, but are not limited to, beta-interferons, corticosteroids, non-steroid anti-inflammatory drugs, tumor necrosis alpha blockers, antimalarial drugs, cyclosporines, tumor necrosis alpha inhibitors, immunosuppressants, immunomodulators, antibody therapeutics, cell-based therapies and T cell epitopes (e.g., ToleroTrans Transplant Rejection Therapy by Circassia, etc.).

BRIEF DESCRIPTION OF THE DRAWINGS

FIG. 1. Amino acid sequence alignment of human (SEQ ID NO: 1, amino acids 20-223 of Genbank Accession No. NP_001630), *Gallus gallus* (SEQ ID NO: 2, amino acids 20-227 of Genbank Accession No. NP_001034653), *Bos taurus* (SEQ ID NO: 3, amino acids 20-224 of Genbank Accession No. AAI02624), and *Cricetulus migratorius* (SEQ ID NO: 4, amino acids 20-223 of Genbank Accession No. AAB28726), serum amyloid P polypeptides (signal sequence not depicted). Amino acids identical to the human SAP are shaded.

FIG. 3. Cytokine generation in splenocyte culture from cells isolated and simulated with aspergillus antigen and treated in vitro and in vivo with hSAP. Spleen cells were isolated from animals 15 days (A) or 30 days (B) after intratracheal conidia challenge. Animals were treated in vivo with hSAP (8 mg/kg, q2d, intranasal; filled bars) or PBS control (q2d, intranasal; open bars) for the last two weeks of the model.

DETAILED DESCRIPTION OF THE INVENTION

Overview

Figure 2A:
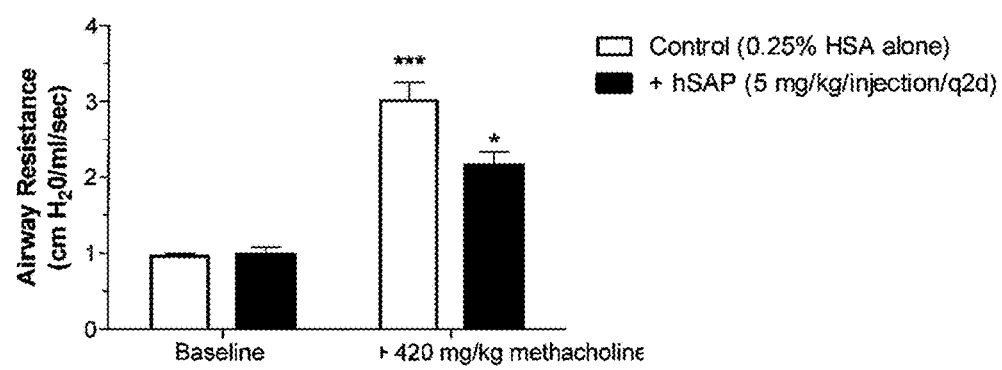
FIG. 2. Exogenous SAP therapy prevented and reversed established airway hyperresponsiveness in a fungal asthma model. *A. fumigatus*-sensitized and conidia-challenged C57BL/6 mice received PBS, or hSAP via intraperitoneal injection every other day from days 0-15 (A) or 15-30 (B) after conidia, and airway resistance was measured following methacholine challenge using invasive airway resistance analysis (Buxco). Data are mean±SEM, n=5 mice/group. *$P<0.05$, ***$P<0.001$ compared with baseline airway resistance in the appropriate treatment group.

Regulatory T cells are a subset of T cells that suppress the activity of effector T cells, as well as other cell types involved in both innate and adaptive immunity (Shevach, E M. 2006. Immunity 25: 195-201). One of the main functions of regulatory T cells is to protect the host against self-antigens, thus limiting autoimmunity. Moreover, certain autoimmune diseases, including diabetes, multiple sclerosis, rheumatoid arthritis and juvenile idiopathic arthritis, result from defects in either the T cell number or function (Baecher-Allan et al. 2006 Immunological reviews 212: 203-216). In fact, IPEX (immune dysregulation poly-endocrinopathy, X-linked syndrome) is the result of a mutation of FoxP3, a key transcription factor expressed by regulatory T cells (Baecher-Allan et al. 2003. Novartis foundation symposium 252: 67-91; Fontenot et al. 2003. Nature immunology 4: 330-336). A current therapeutic strategy to treat autoimmune disorders is adoptive transfer of regulatory T cells that have been purified and expanded in vitro into a patient. This disclosure demonstrates that administration of serum amyloid P (SAP) protein in vivo results in an expansion of suppressor T cells that are efficacious at treating T cell-mediated disease. This disclosure provides new therapeutic approaches for expanding regulatory T cells (in vivo or ex vivo) to treat or prevent diseases where aberrations in regulatory T cell number and/or function have been observed (e.g., autoimmune disorders, graft-versus-host disease, etc.).

SAP is a naturally-occurring serum protein in mammals composed of five identical subunits or protomers which are non-covalently associated in a disc-like molecule. SAP is a 125,000 Dalton pentameric glycoprotein composed of five, non-covalently linked, 25,000 Dalton protomers. SAP belongs to the pentraxin superfamily of proteins, characterized by this cyclic pentameric structure. The classical short pentraxins include SAP as well as C-reactive protein (Osmand, A. P., et al., Proc. Nat. Acad. Sci., 74:739-743 (1977)). SAP is synthesized in the liver and the physiological half-life of human SAP is 24 hours. The sequence of the human SAP subunit is depicted in SEQ ID NO: 1 (amino acids 20-223 of Genbank Accession No. NP_001630, signal sequence not depicted). Previous work has demonstrated that SAP binds to Fc receptors for IgG (FcγR). SAP binding to FcγR provides an inhibitory signal for fibrocyte, fibrocyte precursor, myofibroblast precursor, and/or hematopoetic monocyte precursor differentiation.

Definitions

As used herein, the terms "treatment", "treating", and the like, refer to obtaining a desired pharmacologic and/or physiologic effect. The effect may be prophylactic in terms of completely or partially preventing a disorder or symptom thereof and/or may be therapeutic in terms of a partial or complete cure for a disorder (e.g., autoimmune disease) and/or adverse affect attributable to the disorder. "Treatment", as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

As used herein, a therapeutic that "inhibits" a disorder or condition is a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein the terms "subject" and "patient" refer to animals including mammals, including humans. The term "mammal" includes primates, domesticated animals including dogs, cats, sheep, cattle, horses, goats, pigs, mice, rats, rabbits, guinea pigs, captive animals such as zoo animals, and wild animals.

As used herein the term "tissue" refers to an organ or set of specialized cells such as skin tissue, lung tissue, kidney tissue, and other types of cells.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a desired effect at a reasonable benefit/risk ratio applicable to such treatment.

The term "immune response" refers to host responses to foreign or self antigens. The term "aberrant immune responses" refers to the failure of the immune system to distinguish self from non-self or the failure to respond to foreign antigens. In other words, aberrant immune responses are inappropriately regulated immune responses that lead to patient disorders including autoimmune responses and hyper-responsiveness to foreign antigens. "Inappropriately regulated" can mean inappropriately induced, inappropriately suppressed and/or non-responsiveness.

As used herein, an "autoimmune disease" is a disease or disorder arising from and directed at an individual's own tissues. Examples of autoimmune diseases or disorders include, but are not limited to type I diabetes, multiple sclerosis, rheumatoid arthritis, psoriatic arthritis, autoimmune myocarditis, pemphigus, celiac disease, myasthenia gravis, Hashimoto's thyroiditis, Graves' disease, Addison's disease, autoimmune hepatitis, chronic Lyme arthritis, familial dilated cardiomyopathy, juvenile dermatomyositis, polychondritis, Sjogren's syndrome, psoriasis, juvenile idiopathic arthritis, inflammatory bowel disease, systemic lupus erythematosus, and graft-versus-host disease.

As used herein, the term "nucleic acid" refers to polynucleotide such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotide.

The terms "peptides", "proteins" and "polypeptides" are used interchangeably herein. The term "purified protein" refers to a preparation of a protein or proteins that are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

The terms "compound", "test compound", and "active agent" are used herein interchangeably and are meant to include, but are not limited to, polypeptides, nucleic acids, small molecules and antibodies. "Small molecule" as used herein, is meant to refer to a molecule that has a molecular weight of less than about 5 kD and most preferably less than about 2.5 kD, or even less than 1 kD. Small molecules can be nucleic acids, peptides, polypeptides, peptidomimetics, carbohydrates, lipids or other organic (carbon-containing) or inorganic molecules (including, but not limited to, metals and organometallic compounds). Many pharmaceutical companies have extensive libraries of chemical and/or biological mixtures comprising arrays of small molecules, often fungal, bacterial, or algal extracts, which can be screened with any of the assays of the disclosure.

Treatment Methods

One aspect of the disclosure provides methods for treating or preventing an autoimmune disorder or condition in a patient by administering a therapeutically effective amount of an SAP agonist to a patient in need thereof. The examples of the disclosure demonstrate that administration of SAP to a mammal results in expansion of regulatory T cells as determined by an increase in FoxP3$^+$ cells and enhanced T cell-mediated suppression of effector T cell activity (See, e.g., FIG. 3). As many autoimmune diseases in humans are associated with low numbers of regulatory T cells and/or reduced regulatory T cell function, preferential expansion of regulatory T cells over autoreactive effector T cells promises a substantial therapeutic benefit to patients afflicted with autoimmune disorders. The present disclosure teaches methods of administering SAP agonists to promote regulatory T cell-mediated suppression of autoimmune disorders or conditions.

In some embodiments, administration of an SAP agonist reduces the number of days a patient is afflicted with an autoimmune disorder by at least 1, 2, 3, 4, 5, 6, 7, 8, 9, 10, 15, or more days. In some embodiments, administration of an SAP agonist inhibits the onset of an autoimmune disorder in a patient by at least 1, 2, 3, 4, 5, 6, 7, 8, 9, 10, 15 or more days.

While the method of the invention can be used to treat patients afflicted with an autoimmune disorder, in some embodiments, the methods are also applied to patients who do not have, but are at risk of developing an autoimmune response. In patients at risk of developing an autoimmune disorder, treatment according to the methods of the disclosure can reduce the number of days a patient is afflicted with or inhibit the onset of an autoimmune disorder by at least 1, 2, 3, 4, 5, 6, 7, 8, 9, 10, 15, or more days. In some embodiments, treatment according to the methods of the disclosure prevents an autoimmune disorder in a patient at risk for developing such a disease.

In certain aspects of the disclosure, an SAP agonist is administered to a patient before, during, and/or after treatment with a therapy that causes an autoimmune response or puts a patient at risk for developing such a disorder. In some embodiments, the autoimmune disorder is graft-versus-host disease.

Another aspect of the disclosure provides methods for treating autoimmune disorders by conjoint administration of multiple SAP agonists. As used herein, the term "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in separate formulations, either concomitantly or sequentially. Thus, an individual who receives such treatment can benefit from a combined effect or different therapeutic compounds.

Another aspect of the disclosure provides methods for treating autoimmune-related disorders by conjoint administration of one or more SAP agonists and at least one additional active agent. Active agents of the invention may include, but are not limited to beta-interferons, corticosteroids, non-steroid anti-inflammatory drugs, tumor necrosis blockers, antimalarial drugs, cyclosporines, tumor necrosis alpha inhibitors, immunosuppressants, immunomodulators, cytokines, anti-graft-rejection therapeutics, cell-based therapeutics, vitamin D3, dexamethasone and antibody therapeutics. Cytokines suitable for conjoint administration may include, but are not limited to, IL-2, IL-4, IL-10, TGF-β, IL-15 and/or IL-17. In some embodiments, the additional active agent is a therapeutic agent used to treat or prevent an autoimmune disease.

In one aspect, the present disclosure provides methods for producing a population of cells enriched for regulatory T cells from a sample containing T cells. In some embodiments, the methods for producing a population of cells enriched for regulatory T cells are effected in vivo. In some embodiments, the method comprises obtaining a sample from a mammalian subject that comprises T cells (e.g., CD4+ cells) and contacting the T cells with SAP for a period of time sufficient to generate regulatory T cells. In some embodiments, the T cells are isolated from the mammalian sample prior to exposure to SAP. In some embodiments, the regulatory T cells are isolated from the other cells in the culture after exposure to SAP. In some embodiments, a patient is administered SAP prior to obtaining a biological sample that contains T cells from the patient.

The term "isolated" with respect to T cells refers to cell population preparation in a form that has at least 70, 80, 90, 95, 99, or 100% T cells. In some embodiments, these T cells may be 70, 80, 90, 95, 99, or 100% FoxP3$^+$ and/or IL-10 producing regulatory T cells. In some aspects, a desired cell population is isolated from other cellular components, in some instances to specifically exclude other cell types that may "contaminate" or interfere with the study of the cells in isolation. It is to be understood, however, that such an "isolated" cell population may incorporate additional cell types that are necessary for cell survival or to achieve the desired results provided by the disclosure. For example, antigen presenting cells, such as monocytes (macrophages) or dendritic cells, may be present in an "isolated" cell population of T cells or added to a population of isolated T cells for generation of regulatory T cells. In some aspects, these antigen presenting cells may be activated monocytes or dendritic cells. In some aspects the antigen presenting cells are activated by exposure to a stimulating antigen and/or SAP agonists.

Mammalian T cells for use in the methods of the disclosure may be isolated from a biological sample taken from a mammalian subject. The sample may originate from a number of sources, including, but not limited to peripheral blood, leukapheresis blood product, apheresis blood product, bone marrow, thymus, tissue biopsy, tumor, lymph node tissue, gut associated lymphoid tissue, mucosa associated lymphoid tissue, cord blood, liver, sites of immunologic lesions (e.g., synovial fluid), pancreas, and cerebrospinal fluid. The donor subject is preferably human, and can be fetal, neonatal, child, adult, and may be normal, diseased, or susceptible to a disease of interest. In some embodiments, the mammal is administered SAP prior to isolating the biological sample.

In some embodiments, the T cell sample comprises peripheral blood mononuclear cells (PBMCs) from a blood sample. By "peripheral blood mononuclear cells" or "PBMCs" is meant lymphocytes (including T-cells, B-cells, NK cells, etc.) and monocytes. In general, PBMCs are isolated from a patient using standard techniques. In some embodiments, only PBMCs are taken, either leaving or returning substantially all of the red blood cells and polymorphonuclear leukocytes to the donor. PBMCs may be isolated using methods known in the art, such as leukophoresis. In general, a 5 to 7 liter leukophoresis step is performed, which essentially removes PBMCs from a patient, returning the remaining blood components. Collection of the sample is preferably performed in the presence of an anticoagulant (e.g., heparin).

The T cell-containing sample comprising PBMCs or isolated T cells can be pretreated using various methods before treatment with SAP or an SAP agonist. Generally, once collected, the cells can be additionally concentrated, if this was not done simultaneously with collection or to further purify and/or concentrate the cells. For example, PBMCs can be partially purified by density gradient centrifugation (e.g., through a Ficoll-Hypaque gradient). Cells isolated from a donor sample are normally washed to remove serum proteins and soluble blood components, such as autoantibodies, inhibitors, etc., using techniques well known in the art. Generally, this involves addition of physiological media or buffer, followed by centrifugation. This may be repeated as necessary. The cells can then be counted, and in general, from $1 \times 10^9$ to $2 \times 10^9$ white blood cells are collected from a 5-7 liter leukapheresis. The purified cells can be resuspended in suitable media or buffer to maintain viability. Suitable solutions for resuspension will generally be a balanced salt solution (e.g., normal saline, PBS, Hank's balanced salt solution, etc.) optionally supplemented with fetal calf serum, BSA, HSA, normal goat serum, and/or other naturally occurring factors, in conjunction with an acceptable buffer at low concentration, generally from 5-50 mM. Convenient buffers include, but are not limited to HEPES, phosphate buffers, lactate buffers, etc.

A specific cell type (e.g., effector T cells, regulatory T cells, etc.) can be separated from a complex mixture of cells using techniques that enrich for cells having the desired characteristic (e.g., CD4+, FoxP3+, etc.). Most standard separation methods use affinity purification techniques to obtain a substantially isolated cell population. Techniques for affinity separation may include, but are not limited to, magnetic separation (e.g., using antibody-coated magnetic beads), affinity chromatography, cytotoxic agents joined to a monoclonal antibody (e.g., complement and cytotoxins), and "panning" with antibody attached to a solid matrix. Techniques providing accurate separation include fluorescence activated cell sorting, which can have varying degrees of sophistication, such as multiple color channels, impedance channels, etc. The living cells may be selected against dead cells by employing dyes that associate with dead cells (e.g., propidium iodide, LDS, etc.). Any technique may be used that is not unduly detrimental to the viability of the selected cells.

The affinity reagents used may be specific receptors or ligands for cell surface molecules (e.g., CD4, CD25, etc.). Antibodies may be monoclonal or polyclonal and may be produced by transgenic animals, immunized animals, immortalized B-cells, and cells transfected with DNA vectors encoding the antibody. Details of the preparation of antibodies and their suitability for use as specified binding members are well-known to those skilled in the art. In addition to antibody reagents, peptide-MHC antigen and T cell receptor pairs may be used, as well as peptide ligands, effector and receptor molecules.

Antibodies used as affinity reagents for purification are generally conjugated with a label for use in separation. Labels may include magnetic beads (which allow for direct separation), biotin (which can be removed with avidin or streptavidin bound to a support), fluorochromes (which can be used with a fluorescence activated cell sorter), or other such labels that allow for ease of separation of the particular cell type. Fluorochromes may include phycobiliproteins, such as phycoerythrin and allophycocyanins, fluorescein and Texas red. Frequently, each antibody is labeled with a different fluorochrome to permit independent sorting for each marker.

For purification of a desired cell population, cell-specific antibodies are added to a suspension of cells and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody (i.e., using a saturating amount of antibody). The appropriate concentration can also be determined by titration. The medium in which the cells are separated will be any medium that maintains the viability of the cells. A preferred medium is phosphate buffered saline containing from 0.1% to 0.5% BSA. Various media are commercially available and may be used according to the nature of the cells, including Dulbecco's Modified Eagle Medium, Hank's Basic Salt Solution, Dulbecco's phosphate buffered saline, RPMI, Iscove's medium, PBS with 5 mM EDTA, etc., optionally supplemented with fetal calf serum, BSA, HSA, etc.

The staining intensity of cells can be monitored by flow cytometry, where lasers detect the quantitative levels of fluorochrome (which is proportional to the amount of cell surface antigen bound by the antibodies). Flow cytometry, or fluorescent activated cell sorting (FACS), can also be used to separate cell populations based on the intensity of antibody staining, as well as other parameters such as cell size and light scatter. Although the absolute level of staining may differ with a particular fluorochrome and antibody preparation, the data can be normalized to a control.

The labeled cells are then separated as to the expression of designated marker (e.g., CD4, CD25, etc.). The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Cell populations highly enriched for a desired characteristic (e.g., CD4+ T cells, CD4+CD25+ regulatory T cells, etc.) are achieved in this manner. The desired population will be at or about 70% or more of the cell composition, and usually at or about 90% or more of the cell composition, and may be as much as about 95% or more of the cell population. The enriched cell population may be used immediately. Cells can also be frozen, although it is preferable to freeze cells prior to the separation procedure. Alternatively, cells may be frozen at liquid nitrogen temperatures and stored for long periods of time, being thawed and capable of being reused. The cells will usually be stored in DMSO and/or FCS, in combination with medium, glucose, etc. Once thawed, the cells may be expanded by use of growth factors, antigen, stimulation, antigen presenting cells (e.g., dendritic cells), etc. for proliferation and differentiation.

In some aspects, the present methods are useful for ex vivo generation of regulatory T cells for transplantation into a patient or development of in vitro models and assays for regulatory T cell function. The regulatory T cell cultures serve as a valuable source of novel regulatory factors and pharmaceuticals. Common autoimmune therapeutics are used to block the terminal events of tissue damage but generally do not alter the underlying autoimmune response. While not wishing to be bound by theory, the strategy of the methods disclosed herein is to produce remission by restoring normal regulatory cell function and thus "resetting" the immune system using regulatory T cells made according to the disclosure herein.

Once the PBMCs or isolated T cells have undergone any necessary pre-treatment, the cells are treated with SAP. By "treated" herein is meant that the cells are incubated in a suitable nutrient medium with SAP for a time period sufficient to produce regulatory T cells having the capacity to inhibit immune responses mediated by effector T cells. In some embodiments, the first culture is diluted with about an equal volume of nutrient medium. In other aspects, a first cell culture is divided into two or more portions that are then diluted with nutrient medium. The advantage of culture division is that the cell clusters formed in the first culture (thousands of cells) are mechanically disrupted and form smaller cell clusters (tens to hundreds of cells) during division of the first culture. These small clusters are then able to grow into larger clusters during the next growth period. A cell culture produced in this fashion may be subcultured two or more times using a similar method. In some embodiments, the second culture or any subsequent culture is substantially free of SAP, for example, the culture may contain less than 10 µg/ml, preferably less than 0.1 µg/ml, or more preferably less than 0.001 µg/ml. A culture that is substantially free of SAP is one in which the concentration of SAP is not sufficient to promote the generation of regulatory T cells.

A cell population may be grown in vitro under various culture conditions. Culture medium may be liquid or semi-solid (e.g., containing agar, methylcellulose, etc.) The cell population may be conveniently suspended in any appropriate nutrient medium, including but not limited to Iscove's modified Dulbecco's medium, or RPMI-1640, normally supplemented with fetal calf serum (about 5-10%), L-glutamine, and antibiotics (e.g., penicillin and streptomycin).

The cell culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Specific growth factors that may be used in culturing the subject cells include the interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, etc.) and antigens (e.g., peptide antigens, protein antigens such as alloantigens) preferably in combination with antigen presenting cells, lectins, non-specific stimuli (e.g., Con A; LPS; etc.). The culture may also contain antibodies (e.g. anti-CD3), or specific ligands (in the form of purified ligand, Fc fusion proteins, or other recombinant tagged forms like leucine zipper forms) for cell surface receptors that may stimulate or inhibit regulatory T cell activity. For example, mAb or ligands that bind TNFR or other co-stimulatory molecules on regulatory T cells and could stimulate and increase regulatory T cell activity, override regulatory T cell activity (and induce proliferation), or that stimulate apoptosis of regulatory T cell can be included. The specific culture conditions are typically chosen to achieve a particular purpose (i.e., maintenance of regulatory T cell activity, expand the regulatory T cell population, etc.). The regulatory T cell may be co-cultured with immature or mature dendritic cells, as well as other antigen presenting cells (e.g., monocytes, B cells, macrophages, etc.) prior to, during, or after treatment with SAP. The regulatory T cells may be co-cultured with other T cell populations. In some aspects, the culture also contain vitamin D3 and/or Dexamethasone, which have demonstrated to promote the generation of IL-10-producing regulatory CD4+ T cells (Barrat et al. J. Exp. Med. 195(5): 2002, 603-616).

Genes may be introduced into the regulatory T cells prior to culture or transplantation for a variety of purposes (e.g., prevent or reduce susceptibility to infection, replace genes having a loss of function mutation, increase regulatory T cell potency to inhibit Th cells, to make regulatory T cell home to specific regions in vivo, etc.). Alternatively, vectors may be introduced that express antisense mRNA or ribozymes, thereby blocking expression of an undesired gene. Other methods of gene therapy include the introduction of drug resistance genes to enable transplanted cells to have an advantage and be subject to selective pressure, for example the multiple drug resistance gene (MDR), or anti-apoptosis genes, such as bcl-2. Various techniques known in the art may be used to transfect the target cells (e.g., electroporation, calcium precipitated DNA, fusion, transfection, lipofection, etc). The particular manner in which the DNA is introduced is not critical to the practice of the invention provided it does not affect the viability of the cells.

Many vectors useful for transferring exogenous genes into mammalian cells are available. The vectors may be episomal (e.g., plasmids, virus derived vectors such cytomegalovirus, adenovirus, etc.) or may be integrated into the target cell genome, through homologous recombination or random integration (i.e., retrovirus, including lentivirus-derived vectors such MMLV, HIV-1, ALV, etc.).

In some embodiments, regulatory T cells generated by the methods of the disclosure may be transplanted or reintroduced back into the patient. Methods for adoptive transfer of regulatory T cells are well described in the art, for example, see US Patent Applications 2006/0115899, 2005/0196386, 2003/0049696, 2006/0292164, and 2007/0172947 (the contents of which are hereby incorporated by reference). Therefore, a skilled practitioner would easily be able to transplant or reintroduce the regulatory T cells produced by the methods of the present disclosure into a patient in need thereof.

Transplanted T cells may originate from a T cell-containing sample obtained from the patient himself or from another donor not receiving treatment. This is generally done as is known in the art and usually comprises injecting, or other methods of introducing, the treated cells back into the patient via intravenous administration. For example, the cells may be placed in a 50 ml Fenwall infusion bag by injection using sterile syringes or other sterile transfer mechanisms. The cells can then be immediately infused via IV administration over a period of time, into a free flow IV line into the patient. In some aspects, additional reagents such as buffers or salts may be added as well.

In some embodiments, regulatory T cells generated by the methods of the disclosure may be used to treat or prevent an autoimmune disorder or condition in a patient by administering a therapeutically effective amount of the regulatory T cells to a patient in need thereof. Regulatory T cells of the disclosure can promote regulatory T cell-mediated suppression of autoimmune disorders or conditions. In some embodiments, administration of regulatory T cells, generated by the methods of the disclosure, reduces the number of days a patient is afflicted with an autoimmune disorder by at least 1, 2, 3, 4, 5, 6, 7, 8, 9, 10, 15, or more days. In some embodiments, administration of regulatory T cells, generated by the methods of the disclosure, inhibits the onset of an autoimmune disorder in a patient by at least 1, 2, 3, 4, 5, 6, 7, 8, 9, 10, 15 or more days.

While the methods of the invention can be used to treat patients afflicted with an autoimmune disorder, in some embodiments, the methods are also applied to patients who do not have, but are at risk of developing an autoimmune response. In patients at risk of developing an autoimmune disorder, treatment with regulatory T cells, generated by the methods of the disclosure, can reduce the number of days a patient is afflicted with or inhibit the onset of an autoimmune disorder by at least 1, 2, 3, 4, 5, 6, 7, 8, 9, 10, 15, or more days. In some embodiments, treatment with regulatory T cells, generated by the methods of the disclosure, prevents an autoimmune disorder in a patient at risk for developing such a disease.

In certain aspects of the disclosure, regulatory T cells are administered to a patient before, during, and/or after treatment with a therapy that causes an autoimmune response or puts a patient at risk for developing such a disorder. In certain embodiments, the autoimmune response is an adverse immune response in a patient that has undergone, or will undergo, an organ or tissue transplant (e.g., graft-vs-host disease). Administration of regulatory T cells to a patient in need thereof may be used to treat or prevent graft-vs-host disease as the result of any organ (e.g., kidney, heart, lung, liver, pancreas, corneal tissue, etc.) or tissue (e.g., blood, bone marrow, etc.). Regulatory T cells may be administered before and/or after transplantation (e.g., at least one day before transplantation, from one to five days after transplantation, etc.). In some embodiments, regulatory T cells are administered on a periodic basis before and/or after transplantation.

Another aspect of the disclosure provides methods for treating autoimmune-related disorders by conjoint administration of regulatory T cells and at least one additional active agent. In some embodiments, the additional active agent is a therapeutic agent used to treat or prevent an autoimmune disease. Active agents of the invention may include, but are not limited to, beta-interferons, corticosteroids, non-steroid anti-inflammatory drugs, tumor necrosis blockers, antimalarial drugs, cyclosporines, tumor necrosis alpha inhibitors, immunosuppressants, immunomodulators, cytokines, antigraft-rejection therapeutics, vitamin D3, Dexamethasone, antibody therapeutics, and T cell epitopes (e.g., ToleroTrans Transplant Rejection Therapy by Circassia, etc.). Cytokines suitable for conjoint administration may include, but are not limited to IL-2, IL-4, IL-7, IL-10, TGF-β, IL-15 and/or IL-17. In some embodiments the additional active agent may be a cell population comprising other cell types than regulatory T cells. For example, regulatory T cells may be conjointly administered to a patient in need thereof with one or more antigen presenting cell types, such as monocytes or dendritic cells. In some aspects, these antigen presenting cells may be activated monocytes or dendritic cells. In some aspects the antigen presenting cells are activated by exposure to a stimulating antigen and/or SAP agonists. In some embodiments, the additional active agent may be an SAP agonist. In certain aspects, methods for treating autoimmune-related disorders comprise the conjoint administration of regulatory T cell, at least one SAP agonist, and one or more additional active agents. The additional active agents may be administered on a periodic basis.

Any treatment method of the disclosure may be repeated as needed or required. For example, the treatment may be done on a periodic basis. The frequency of administering treatment may be determined by one of skill in the art. For example, treatment may be administered once a week for a period of weeks, or multiple times a week for a period of time (e.g., 3-5 times over a two week period). Generally, the amelioration of the autoimmune disease symptoms persists for some period of time, preferably at least months. Over time, the patient may experience a relapse of symptoms, at which point the treatments may be repeated.

After transplanting the cells into the patient, the effect of the treatment may be evaluated, if desired. One of skill in the art would recognize there are many methods of evaluating immunological manifestations of an autoimmune disease (e.g., quantification of total antibody titers or of specific immunoglobulins, renal function tests, tissue damage evaluation, etc.). Tests of T cells function such as T cell numbers, phenotype, activation state and ability to respond to antigens and/or mitogens also may be done.

The disclosure also provides kits for treating or preventing autoimmune-related disorders that comprise one or more SAP agonists. In some embodiments, the kit may include an additional active agent to be administered conjointly with one or more SAP agonists. In some embodiments the additional agent is a therapeutic agent used to treat or prevent an autoimmune disease. Active agents of the invention may include, but are not limited to beta-interferons, corticosteroids, non-steroid anti-inflammatory drugs, tumor necrosis blockers, antimalarial drugs, cyclosporines, tumor necrosis alpha inhibitors, immunosuppressants, immunomodulators, cytokines, anti-graft-rejection therapeutics, and antibody therapeutics. Cytokines suitable for conjoint administration may include, but are not limited to IL-2, IL-4, IL-10, TGF-β, IL-15 and/or IL-17. In certain aspects, the additional active agent is a population of regulatory T cells. The agonist(s) and additional active agents may be formulated to be administered conjointly. The active agents of the kit may be administered separately or in a combination formulation. The active agents may be administered simultaneously or at different dosing schedules.

In some embodiments, the invention further provides kits for the practice of the methods of the invention (i.e., the incubation of cells with the SAP agonist to generate regulatory T cells). The kit may have a number of components. In some aspects, the kit may comprise a cell treatment container that is adapted to receive cells from a patient. The patient may be a normal donor or a patient afflicted with an autoimmune disorder or other condition. The container should be sterile. In some embodiments, the cell treatment container is used for collection of the cells, for example it is adaptable to be hooked up to a leukopheresis machine using an inlet port. In other embodiments, a separate cell collection container may be used. The kit may also be adapted for use in an automated closed system to purify specific T cell subsets and expand them for transfer back to the patient.

The form and composition of the cell treatment container may vary, as will be appreciated by those in the art. Generally the container may be in a number of different forms, including a flexible bag, similar to an IV bag, or a rigid container similar to a cell culture vessel. It may be configured to allow stirring. Generally, the composition of the container will be any suitable, biologically inert material (e.g., glass or plastic, e.g., polypropylene, polyethylene, etc.) The cell treatment container may have one or more inlet or outlet ports, for the introduction or removal of cells, reagents, regulatory compositions, etc. For example, the container may comprise a sampling port for the removal of a fraction of the cells for analysis prior to reintroduction into the patient. Similarly, the container may comprise an exit port to allow introduction of the cells into the patient; for example, the container may comprise an adapter for attachment to an IV setup.

The kit further comprises at least one dose of a composition comprising a SAP agonist and optionally one or more additional active agent (e.g., cytokines, mitogens, etc.). The components may be used as separate doses or combined. For example, SAP can be combined with at least one or more cytokines and/or one or more mitogens. The kit may also contain at least one dose of a second regulatory composition containing one or more cytokines (e.g., IL-2, IL-7, IL-10, IL-15, IL-17, etc.), mitogens or additional active agents. In some embodiments, the additional active agent may be a therapeutic agent used to treat or prevent an autoimmune disease. Active agents of the kit may include, but are not limited to beta-interferons, corticosteroids, non-steroid anti-inflammatory drugs, tumor necrosis blockers, antimalarial drugs, cyclosporines, tumor necrosis alpha inhibitors, immunosuppressants, immunomodulators, cytokines, anti-graft-rejection therapeutics, and antibody therapeutics. Cytokines suitable for administration may include, but are not limited to IL-2, IL-4, IL-10, TGF-β, IL-15 and/or IL-17 autoimmune therapeutic.

The kit may also contain at least one dose of nutrient media for diluting the first culture and/or to dissolve lyophilized kit components. "Dose" in this context means an amount of the composition that is sufficient to cause an effect (i.e., SAP agonist-induced expansion of regulatory T cells). In some cases, multiple doses may be included. In one embodiment, the dose may be added to the cell treatment container using a port; alternatively, in a preferred embodiment, the first regulatory composition is already present in the cell treatment container. In some embodiments, the regulatory compositions and/or nutrient media are lyophilized for stability, and are reconstituted using nutrient media, or other reagents. In some embodiments, the kit may additionally comprise at least one reagent, including buffers, salts, media, proteins, drugs, etc. For example, mitogens, monoclonal antibodies and treated magnetic beads for cell separation can be included. In some embodiments, the kit may additionally comprise written instructions for using the kits.

Autoimmune Disorders

The pathogenesis of a number of autoimmune diseases is believed to be caused by autoimmune T cell responses to self-antigens present in the organism. For example, autoreactive T cells have been implicated in the pathogenesis of: type I diabetes, multiple sclerosis, rheumatoid arthritis, psoriatic arthritis, autoimmune myocarditis, pemphigus, celiac disease, myasthenia gravis, Hashimoto's thyroiditis, Graves' disease, Addison's disease, autoimmune hepatitis, chronic Lyme arthritis, familial dilated cardiomyopathy, juvenile dermatomyositis, polychondritis, Sjogren's syndrome, psoriasis, juvenile idiopathic arthritis, inflammatory bowel disease, systemic lupus erythematosus, and graft-versus-host disease.

The importance of regulatory T cells in the protection from autoimmunity has been demonstrated in various animal models. For example, depletion of CD4+CD25+ regulatory T cells from mice produces a spectrum of spontaneous organ-specific autoimmune manifestations and increases the susceptibility to induction of autoimmune diseases such as collagen-induced arthritis (Sakaguchi et al., J. Exp. Med. 161:72-87, 1985; Morgan et al., Arthritis Rheum. 48:1452-1460, 2003). Moreover, studies have demonstrated that autoimmune diseases can be ameliorated by the addition of regulatory T cells. It has been shown that regulatory T cell therapy can effectively delay and/or treat animals in a variety of immunological disease models, including diabetes, colitis, gastritis and graft-versus-host disease (Salomon et al., Immunity, 12:431-440, 2000; Read et al., J. Exp. Med., 192:295-302, 2000; Taylor et al., Blood 99:3493-3499, 2002; Hoffman et al., J. Exp. Med 196:389-399, 2002; and Edinger et al., Nat. Med. 9:1144-1150, 2003).

In humans, the ability of regulatory T cells to modulate the activity of T cells in an antigen-specific manner has been demonstrated in the context of various diseases, including regulation of T cells specific to tumor antigens (Viguier et al., J. Immunol. 173:1444-1453, 2004); alloantigens in the setting of bone marrow transplantation (Ng et al., Blood 98:2736-2744, 2001); and the foreign antigen HA (Walker et al., PNAS 102:4103-4108, 2005). Therefore, immunotherapy with regulatory T cells is useful in the context of a cellular therapy for regulating the immune response in the subject.

In some embodiments, regulatory T cells generated by the methods of the disclosure and/or SAP agonists are used to prevent or treat a disease or condition, including autoimmune diseases, inflammatory diseases, or transplant rejection as a consequence of graft-versus-host response. In certain embodiments, regulatory T cells and/or SAP agonists are conjointly administered with one or more additional active agents. In certain embodiments, these additional active agents may be therapeutic agents used to treat or prevent autoimmune disease. Any therapeutic agent or treatment method used to treat or prevent an autoimmune disorder may be used as part of a conjoint therapy with administration of regulatory T cell generated by the methods of the disclosure and/or SAP agonists. For each autoimmune indication described herewithin, the most prevalent therapeutic agents or treatment methods have been described. While not wishing to be bound by theory or limited to the agents specified, any of these therapeutic agents may be used as a suitable conjoint therapeutic.

Type I Diabetes

Type I diabetes (T1DM) is an autoimmune disease mediated by the destruction of islet cells, the insulin-producing β-cells of the pancreas. This destruction represents a loss of immune tolerance and is due to pathogenic CD4+ and CD8+ T and B cell responses directed against proteins found in the pancreas. In humans, several studies have identified abnormalities in the number or function of regulatory T cells in patients with T1DM (Kukreja et al., J. Exp. Med. 199:1285-1291, 2004; Kriegel et al., J. Exp. Med. 199:1285-1291, 2004). A lack of regulatory T cells is also implicated in the pathogenesis of diabetes by the finding of diabetes in both animals depleted of regulatory T cells and in humans with IPEX (see Wildin et al., Nat. Genet. 27:18-20, 2001). In the NOD mouse model, studies have demonstrated the ability to use islet specific regulatory T cells to protect and treat diabetes (Tang et al., J. Exp. Med 199:1455-1465, 2004; Tarbell et al., J. Exp. Med., 199:1467-1477, 2004).

Treatment for type I diabetes is a lifelong commitment of monitoring blood sugar, taking insulin, maintaining a healthy weight, eating healthy foods and exercising regularly. The goal is to keep the blood sugar level as close to normal as possible to delay or prevent complications. In fact, tight control of blood sugar levels can reduce the risk of diabetes-related heart attacks and strokes by more than 50 percent. Insulin therapy is necessary for the survival of patients afflicted with type I diabetes. Because stomach enzymes interfere with insulin taken by mouth, oral insulin is not a preferred option for lowering blood sugar. Often, insulin is injected using a fine needle and syringe or by an insulin pump. Many types of insulin are available, including rapid-acting insulin, long-acting insulin and intermediate options. Examples include regular insulin (e.g., Humulin R, Novolin R, etc.), insulin isophane (e.g., Humulin N, Novolin N, etc.), insulin lispro (e.g., Humalog), insulin aspart (e.g., NovoLog) and insulin glargine (e.g., Lantus).

Other therapeutics include pramlintide, to slow the movement of food through the stomach to curb the sharp increase in blood sugar that occurs after meals, and low-dose aspirin therapy, which may help prevent heart and blood vessel disease. One potential cure for type 1 diabetes is a pancreas transplant. Other types of transplants currently under investigation for therapeutic efficacy include islet cell transplant and stem cell transplant.

Graft Versus Host Disease (GVHD)

Graft rejection mediated by host T cells is a major problem that is treated by long-term immunosuppression of the transplant recipient. Studies in mice have demonstrated that adoptive transfer of regulatory T cells can block graft-versus-host disease without affecting the graft-versus-leukemia response (Edinger et al., Nat. Med. 9:1144-1150, 2003). Accordingly, in one embodiment, the invention provides a method of reducing the risk of, or the severity of, an adverse immune response in a patient that has undergone, is undergoing, or will undergo, an organ transplant, comprising administering to the patient according to the methods described herein a population of regulatory T cells in an amount effective to reduce the risk or severity of an adverse immune response in the patient. The methods may be applied to solid organ (e.g., kidney(s), heart, lung(s), liver and pancreas, etc.) transplant recipients or to tissue (e.g., blood, bone marrow, etc.) transplant recipients.

The best treatment for GVHD is prevention. Prophylaxis for GVHD usually consists of methotrexate with or without prednisone, cyclosporine, cyclophosphamide, or tacrolimus Topical tacrolimus may be helpful for mucosal disease. Once the diagnosis of GVHD is established, treatment consists of continuing the original immunosuppressive agent and adding methylprednisolone. Chronic GVHD requires continued immunosuppressive therapy plus other modifying agents. Halofuginone, a topically applied inhibitor of collagen type I synthesis, is beneficial in patients with sclerodermatous GVHD. Thalidomide has been used for chronic GVHD with reported benefit, but the high rate of adverse effects (including granulocytopenia) precludes its use in many patients. Monoclonal antibodies directed either against activated T-cells (e.g., daclizumab, visilizumab, murine anti-CD147 monoclonal antibody, etc.) or against cytokines (e.g., infliximab, etanercept, etc.) have had promising preliminary results.

Multiple Sclerosis

The pathogenesis of autoreactive T cells in Multiple Sclerosis (MS) is believed to arise from T cell responses to myelin antigens, in particular to myelin basic protein (MBP). Although MBP-reactive T cells can be isolated from both healthy individuals and MS patients, the T cells isolated from MS patients are found to undergo in vivo activation and occur at higher precursor frequency in blood and cerebrospinal fluid in MS patients. These MBP reactive T cells produce Th1 cytokines, including IL-2, TNF-α and IFN-γ, which facilitate migration of inflammatory cells into the central nervous system and exacerbate myelin-destructive inflammatory responses in MS. Common therapeutics for MS include, but are not limited to, beta interferons (e.g., Avonex, Rebif, etc.), Glatiramer, corticosteroids, muscle relaxants (e.g., tizanidine, baclofen, etc.), and medications to reduce fatigue (e.g., amantadine, modafinil, etc.). In a recent study, ectopic expression of the neural autoantigen myelin basic protein was demonstrated to protect from autoimmune neuroinflammation in a mouse model of multiple sclerosis. Protection from autoimmunity was mediated by MBP-specific CD4+CD25+ regulatory T cells, as demonstrated by the ability of these cells to prevent disease when adoptively transferred into other autoimmune mice and by suppressing conventional CD4+CD25− T cell proliferation after antigen-specific stimulation with myelin basic protein in vitro (Luth et al., The Journal of Clinical Investigation 118(10): 3403-3410, 2008).

Psoriasis and Psoriatic Arthritis

Psoriatic arthritis is a chronic autoimmune disease characterized by inflammation of the skin (psoriasis) and joints (arthritis). Psoriasis is a common skin condition affecting 2% of the Caucasian population in the United States and is characterized by raised, red areas of skin inflammation with scaling. Psoriasis often affects the tips of the elbows and knees, the scalp, the navel, and around the genital areas or anus. Approximately 10% of patients who have psoriasis also develop an associated inflammation of their joints. Psoriatic arthritis is characterized as a systemic rheumatic disease that can also cause inflammation in body tissues away from the joints other than the skin, such as in the eyes, heart, lungs, and kidneys. Psoriatic arthritis shares many features with several other arthritic conditions, such as ankylosing spondylitis, reactive arthritis (formerly Reiter's syndrome), and arthritis associated with Crohn's disease or ulcerative colitis. All of these conditions can cause inflammation in the spine, joints, eyes, skin, mouth, and other organs. In view of their similarities and tendency to cause inflammation of the spine, these conditions are collectively referred to as "spondyloarthropathies".

Currently, there are three basic types of treatments for psoriatic arthritis: topical therapy, phototherapy, and systemic therapy. Initial treatment generally comprises direct application of topical non-steroidal anti-inflammatory drugs (NSAIDs) to areas around affected joints. Other topical therapeutics include corticosteroids (e.g., clobetasol, fluocinolone, betamethasone, etc.), vitamin D-3 derivatives (e.g., calcipotriene, etc., coal tar (DHS Tar, Doak Tar, Theraplex T, etc.), anthralin (Dithranol, Anthra-Derm, Drithocreme, etc.), or retinoids (e.g., Tazarotene). In some instances, phototherapy is used to treat the psoriasis indications of the disease. The ultraviolet (UV) light slows the production of skin cells and reduces inflammation. UV-B therapy is usually combined with one or more topical treatments and can be extremely effective for treating moderate-to-severe plaque psoriasis. UV-B therapy is usually combined with the topical application of corticosteroids, calcipotriene, tazarotene, or creams or ointments that soothe and soften the skin PUVA is another type of phototherapy that combines a psoralen drug, such as methoxsalen, with ultraviolet A (UV-A) light therapy. Psoralen drugs make the skin more sensitive to light and the sun and are taken by mouth several hours before UV-A light therapy.

For severe psoriatic arthritis, patients may be administered systemic therapeutics. These drugs are generally started only after both topical treatment and phototherapy have failed. Systemic therapeutics may include, but are not limited to psoralens (e.g., Methoxsalen, trioxsalen, etc.), etanercept, methotrexate, cyclosporine, alefacept, adalimumab, and infliximab, antimalarial medication (e.g., hydroxychloroquine, injectable gold and oral gold auranofin, sulfasalazine, leflunomide, etc.), TNF-blockers (e.g., etanercept, infliximab, adalimumab, etc.), IL-12 and IL-23 inhibitors (e.g., ustekinumab) and corticosteroids.

Rheumatoid Arthritis

Rheumatoid arthritis (RA) is a chronic disorder that most commonly causes inflammation and tissue damage in joints (arthritis) and tendon sheaths and is associated with anemia. It can also produce diffuse inflammation in the lungs, pericardium, pleura, and the sclera of the eye, and also nodular lesions, most common in subcutaneous tissue under the skin Rheumatoid arthritis is characterized as an autoimmune disease that causes systemic disorders but principally affects synovial tissues. Autoantibodies to IgG-Fc, known as rheumatoid factors (RF), and antibodies to citrullinated peptides (ACPA) are a halmark of rheumatoid arthritis. Although the mechanism is not fully elucidated, disease manifestation is thought to involve abnormal B cell-T cell interaction, with presentation of antigens by B cells to T cells via HLA-DR to elicit production of RF and ACPA autoantibodies. Inflammation is then driven either by B cell or T cell products stimulating release of TNF and other cytokines.

The arthritic symptoms of rheumatoid arthritis are due to synovitis, i.e., inflammation of the synovial membrane that lines joints and tendon sheaths. Joints become swollen, tender and warm, and stiffness prevents their use. With time, RA nearly always affects multiple joints (polyarthritis). Most commonly, small joints of the hands, feet and cervical spine are affected, but larger joints like the shoulder and knee can also be involved. Synovitis can lead to tethering of tissue with loss of movement and erosion of the joint surface, causing deformity and loss of function.

As there is no cure, treatment for RA is directed at reducing inflammation in joints in order to relieve pain and prevent or slow joint damage. Common medications used to treat rheumatoid arthritis include: NSAIDs (e.g., ibuprofen, naproxen sodium, Cox-2 inhibitors, etc.), steroids (e.g., prednisone, methylprednisolone, etc.), disease-modifying antirheumatic drugs (e.g., hydroxychloroquine, the gold compound auranofin, sulfasalazine, minocycline and methotrexate), immunosuppressants (e.g., leflunomide, azathioprine, cyclosporine, cyclophosphamide, etc.), TNF-alpha inhibitors (e.g., tanercept, infliximab, adalimumab, etc.) anakinra, abatacept, and rituximab.

Myocarditis

Myocarditis is an inflammatory disease of the myocardium with a wide range of clinical presentation. It is diagnosed by established histologic, immunologic, and immunochemical criteria. Myocarditis is characterized as an inflammatory infiltrate of the myocardium with necrosis and/or degeneration of adjacent myocytes. It usually manifests in an otherwise healthy person and can result in rapidly progressive (and often fatal) heart failure and arrhythmia. In the clinical setting, myocarditis is synonymous with inflammatory cardiomyopathy Myocarditis is caused by wide variety of infectious organisms, autoimmune disorders, and exogenous agents, with genetic and environmental predisposition. Most cases are presumed to be caused by a common pathway of autoimmune-mediated injury, although direct cytotoxic effects of the causative agent and damages due to cytokine expression in the myocardium may play some role in myocarditis etiology. Myocardial damage has an acute and chronic phase. In the acute stage, myocyte destruction is a direct consequence of the offending agent, which causes cell-mediated cytotoxicity and cytokine release, contributing to myocardial damage and dysfunction. During the chronic phase, there is continued myocyte destruction that is mediated by an autoimmune mechanism, with associated abnormal expression of human leukocyte antigen (HLA) in myocytes. In general, treatment of both acute and chronic myocarditis is aimed at reducing congestion and improving cardiac hemodynamics in heart failure. Treatment of heart failure follows the same treatment regimen regardless of the underlying cause, including administration of ACE inhibitors (e.g., enalapril, etc.), beta-adrenergic blockers, vasodilators (e.g., nitroglycerin, sodium nitroprusside, etc.), and diuretics (e.g., furosemide, etc.). Intensive immunosuppressive therapy (e.g., corticosteroids, azathioprine, cyclosporine, muromonab-CD3/OKT3, etc.) has been shown to have some benefit only in small-scale clinical studies in treatment of giant cell myocarditis.

Autoimmune Hepatitis

Autoimmune hepatitis can develop after viral infections, including acute hepatitis A, hepatitis B, measles, or Epstein-Barr virus. Epstein-Barr is one of the most common human viruses and linked to a number of disorders, including mononucleosis. In autoimmune hepatitis, the host immune system, which ordinarily attacks viruses, bacteria and other pathogens, instead targets the liver. This can lead to chronic inflammation and serious damage to liver cells. Two main forms of autoimmune hepatitis have been identified. Type 1 autoimmune hepatitis often develops suddenly and is the most common type of the disease. Although it can occur in anyone at any age, most of those affected are young women. About half the people with type 1 autoimmune hepatitis have other autoimmune disorders, such as thyroiditis, rheumatoid arthritis or ulcerative colitis. Their blood also is likely to contain antibodies against liver tissue. Although adults can develop type 2 autoimmune hepatitis, it is most common in young girls and often occurs with other autoimmune problems.

Methods of treating autoimmune hepatitis are directed at inhibiting the autoimmune response and slowing the progress of the disease. To achieve this, doctors usually prescribe an initial high dose of the corticosteroid drug prednisone to suppress the immune system. As soon as signs and symptoms improve, the medication is reduced to the lowest possible dose that controls the disease. Although patients may experience remission a few years after starting treatment, the disease usually returns when the drug is discontinued. Prednisone, especially when taken long-term, can cause a wide range of serious side effects. Therefore, azathioprine, another immunosuppressant medication, is sometimes used along with prednisone. This helps lower the amount of prednisone needed, reducing its side effects.

Chronic Lyme Arthritis

Lyme disease pathology is caused by the host immune response to infection with the spirochete *Borrelia burgdorferi*. *B burgdorferi* induces an immune response that may lead to symptoms in various organs, with little evidence of bacterial invasion. Studies of Lyme arthritis have shown that the arthritis is associated with certain immunological factors, including the production of proinflammatory cytokines and the formation of immune complexes, and also genetic factors, such as human leukocyte antigen (HLA)-DR4 and HLA-DR2. Approximately 10% of patients with intermittent arthritis as a result of the infection develop a chronic arthritis. This condition may last for several years and can develop into a destructive arthritis. Generally, Lyme disease is treated with outpatient antibiotics such as doxycycline, amoxicillin, erythromycin, ceftriaxone, cefuroxime, and chloramphenicol. However, patients afflicted with chronic arthritis can be treated with immunosuppressive agents.

Dilated Cardiomyopathy

Dilated cardiomyopathy (DCM) is a disease of the heart muscle characterized by ventricular dilatation and impaired systolic function. DCM is a leading cause of heart failure and arrhythmia. The diagnosis of idiopathic dilated cardiomyopathy is assigned to patients with left ventricular systolic dysfunction and dilatation in the absence of any other documented cause. Idiopathic dilated cardiomyopathy is presumed to have a multifactorial origin, including autoimmune mechanisms. In patients with DCM, a great variety of autoantibodies that react against cardiac antigens have been identified. DCM therapeutics usually affect the physiological functions of the heart, including angiotensin-converting enzyme inhibitors (e.g., captopril, enalapril, lisinopril, etc.), angiotensin receptor blockers (e.g., losartan, valsartan, etc.), diuretics (e.g., furosemide, bemetanide, ethacrynic acid, torsemide, etc.), acetazolamide, aldosterone inhibitors (e.g., spironolactone, eplerenone, vasopressin, etc.), inotrope (e.g., digoxin, etc.), β-adrenergic blockers (e.g., bisoprolol, metoprolol succinate, carvedilol, etc.).

Juvenile Dermatomyositis

Juvenile dermatomyositis (JDM) is an autoimmune disease causing vasculitis that manifests itself in children; it is the pediatric counterpart of dermatomyositis. In JDM, the body's immune system attacks blood vessels throughout the body, causing inflammation called vasculitis. Other forms of juvenile myositis are juvenile polymyositis and juvenile inclusion-body myositis, which are extremely rare and are not as common in children as in adults. The vasculitis caused by JDM manifests itself predominantly in two ways: a pinkish purple rash often associated with calcium deposits under the skin and muscle inflammation. Therapy for dermatomyositis is directed at minimizing both aspects of the disorder. In addition, some patients may need treatment for other systemic manifestations or complications. Common treatments for JDM include systemic administration of glucocorticoids (e.g., prednisone, etc.), immunosuppressive agents (e.g., methotrexate, azathioprine, mycophenolate, sirolimus, rituximab, etc), high-dose intravenous immunoglobulin (e.g., gamimune, gammagard, sandoglobulin, etc.), antimalarial agents (e.g., hydroxychloroquine, chloroquine phosphate, etc.), and calcium channel blockers (e.g., diltiazem, etc.)

Sjogren's Syndrome

Sjogren's syndrome is an autoimmune disease characterized by the abnormal production of autoantibodies in the blood that are directed against various tissues of the body. This particular autoimmune illness features inflammation in certain glands of the body. Inflammation of the glands that produce tears (lacrimal glands) leads to decreased water production for tears and eye dryness. Inflammation of the glands that produce the saliva in the mouth (salivary glands, including the parotid glands) leads to dry mouth and dry lips. Current therapeutics for Sjogren's syndrome include the administration of nonsteroidal anti-inflammatory drugs, corticosteroids, antimalarial drugs (e.g., hydroxychloroquine, etc.), pilocarpine, cevimeline, cyclosporine, and immunosuppressants (e.g., cyclophosphamide, methotrexate, mycophenolate, azathioprine, etc.).

Juvenile Idiopathic Arthritis

Juvenile idiopathic arthritis (JIA) is the term used to describe arthritis inflammation of the synovium, the lining of joints, with onset before 16 years of age. Previously called juvenile rheumatoid arthritis, the name has been changed to reflect the difference between the juvenile and adult forms of arthritis. Oligoarticular (pauciarticular) onset JIA (40-60% of cases) is common in girls with onset around age 2 years. Four or fewer joints are involved during the first 6 months of the disease (often asymmetric). Oligoarticular onset commonly involves the knees and, less frequently, the ankles and wrists. Approximately 75% of these patients test positive for antinuclear antibodies. Polyarticular onset JIA (20-40%) is also common in girls with peak onset observed at age 3 years. It involves 5 or more joints during the first 6 months of the disease and commonly involves the small joints of the hand and, less frequently, the larger joints of the knee, ankle, or wrist. Asymmetric arthritis may be acute or chronic and may be destructive in 15% of patients. Systemic symptoms, including anorexia, anemia, and growth retardation, are moderate. Approximately 40% of these patients test positive for autoantibodies. Systemic onset JIA (10-20%) occurs with equal frequency in boys and girls and can appear at any age. Symmetric polyarthritis is present and may be destructive in 25% of patients. Hands, wrists, feet, ankles, elbows, knees, hips, shoulders, cervical spine, and jaw may be involved. Systemic onset is associated with fever, macular rash, leukocytosis, lymphadenopathy, and hepatomegaly. Pericarditis, pleuritis, splenomegaly, and abdominal pain are less commonly observed. Current therapeutics for JIA include corticosteroids (e.g., prednisolone acetate, triamcinolone acetonide, prednisone, etc.), cycloplegics (e.g., cyclopentolate, homatropine hydrobromide, etc.), nonsteroidal anti-inflammatory drugs (e.g., indomethacin, naproxen, ibuprofen, ketorolac, diclofenac, etc.), immunosuppressives (e.g., etanercept, methotrexate, cyclosporine, cyclophosphamide, chlorambucil, etc), tumor necrosis factor inhibitors (e.g., adalimumab, infliximab, etc.), immunomodulator (e.g., abatacept, etc.).

Systemic Lupus Erythematosus

Systemic lupus erythematosus (SLE) is a chronic inflammatory disease of unknown cause that affects multiple organ systems. The clinical course is marked by spontaneous remissions and relapses. Immunologic abnormalities, especially the production of a number of antinuclear antibodies, are another prominent feature of this disease. Autoantibodies, circulating immune complexes, and T lymphocytes all contribute to the expression of disease. Organ systems affected include the dermis, serous membranes, renal, central nervous system, hematologic, musculoskeletal, cardiovascular, pulmonary, vascular endothelium, and gastrointestinal. Current therapeutics for SLE include nonacetylated salicylates (e.g., choline magnesium trisalicylate, etc.), nonsteroidal anti-inflammatory drugs, antimalarials (e.g., hydroxychloroquine, etc.), glucocorticoids (e.g., prednisone, methylprednisolone, etc.), immunosuppressives/cytotoxic agents (e.g., cyclophosphamide, azathioprine, etc.). Other treatment for SLE include B cell depletion techniques, for example, anti-CD20 antibodies (e.g., rituximab, ofatumumab, IMMU-106, GA-101, etc.), anti-CD22 antibodies (e.g., epratuzumab), TNF-α and IL-6 blockers and antagonists, and inhibitors of complement activation (e.g., eculizumab).

Inflammatory Bowel Disease

The term inflammatory bowel disease covers a group of disorders in which the intestines become inflamed, and it is generally believed to result from an autoimmune reaction against intestinal tissue. Two major types of IBD are described: ulcerative colitis and Crohn's disease. As the name suggests, ulcerative colitis is limited to the colon. Although Crohn's disease can involve any part of the gastrointestinal tract from the mouth to the anus, it most commonly affects the small intestine and/or the colon. Both ulcerative colitis and Crohn's disease are usually variable in the intensity and severity of illness. When there is severe inflammation, the disease is considered to be in an active stage. When the degree of inflammation is reduced or absent, the patient usually is without symptoms and is considered to be in remission. An unknown factor/agent triggers the body's immune system to produce an inflammatory reaction in the intestinal tract that continues without control. As a result of the inflammatory reaction, the intestinal wall is damaged leading to bloody diarrhea and abdominal pain. Factors that can turn on the body's immune system include an infectious agent, an immune response to foreign antigens (e.g., protein from cow milk), or an autoimmune process. As the intestines are continuously exposed to agents that can cause immune reactions, it is thought that the disease results from a failure of the body to turn off normal immune responses. Different groups of drugs are used for the treatment of patients with inflammatory bowel disease, including, but not limited to, aminosalicylates (e.g., sulfasalazine, mesalamine, olsalazine, balsalazide, etc.), corticosteroids (e.g., methylprednisolone, hydrocortisone, prednisone, prednisolone, budesonide, dexamethasone, etc.), immune modifiers (e.g., 6-mercaptopurine, azathioprine, etc.), antitumor necrosis factor agents (e.g., infliximab, etc.), and antibiotics (e.g., metronidazole, ciprofloxacin, etc.). For symptomatic relief, patients are administered antidiarrheal agents, antispasmodics, and acid suppressants.

Polychondritis

Relapsing polychondritis (RP) is a severe, episodic, and progressive inflammatory condition involving cartilaginous structures, predominantly those of the ears, nose, and laryngotracheobronchial tree. Other affected structures may include the eyes, cardiovascular system, peripheral joints, skin, middle and inner ear, and central nervous system. The etiology of this rare disease is unknown; however, the pathogenesis has been characterized as autoimmune. The evidence for an autoimmune etiology includes pathological findings of infiltrating T cells, the presence of antigen-antibody complexes in affected cartilage, cellular and humoral responses against collagen type II and other collagen antigens, and the observation that immunosuppressive regimens most often suppress the disease. The specificity of autoimmune injury to cartilaginous tissues has led investigators to identify autoantibody against cartilage-specific collagen types II, IX, and XI to be present in 30-70% of patients with RP. No controlled trials of therapy for RP have been published. Therefore, the goal of current treatment methods is to abate current symptoms and preserve the integrity of cartilaginous structures. Common therapeutics for RP include, but are not limited to, administration of corticosteroids (e.g., prednisone, etc.), disease-modifying antirheumatic drugs (e.g., methotrexate, etc.), anti-inflammatory agents (e.g., dapsone, etc.), tumor necrosis factor-alpha inhibitors (e.g., infliximab, etanercept, etc.), and immune stimulants/Interleukin 1 inhibitors (e.g., anakinra, etc.).

Pemphigus

Pemphigus is a rare group of autoimmune blistering diseases that affect the skin and mucous membranes. In pemphigus, autoantibodies form against desmoglein, a family of cadherins proteins (DSG1, DSG2, DSG3, and DSG4) that attach adjacent epidermal cells via attachment points called desmosomes. When autoantibodies attack desmogleins, the cells become separated from each other and the epidermis becomes "unglued", a phenomenon called acantholysis. This causes blisters that slough off and turn into sores. In some cases, these blisters can cover a significant area of the skin There are three types of pemphigus which vary in severity: pemphigus vulgaris, pemphigus foliaceus, and paraneoplastic pemphigus. If not treated, pemphigus can be fatal due to overwhelming infection of the sores. The most common treatment is the administration of oral steroids, especially prednisone. The side effects of corticosteroids may require the use of steroid-sparing or adjuvant drugs. The immuno-suppressant CellCept (Mycophenolic acid) is among those being used. Intravenous gamma globulin (IVIG, e.g., gamimune, gammagard, sandoglobulin, etc.) may be useful in severe cases, especially paraneoplastic pemphigus. Mild cases sometimes respond to the application of topical steroids. Recently, Rituximab, an anti-CD20 antibody, was found to improve otherwise untreatable severe cases of Pemphigus vulgaris. If paraneoplastic pemphigus is diagnosed with pulmonary disease, a cocktail of immunosuppressant drugs is sometimes used in an attempt to halt the rapid progression of bronchiolitis obliterans, including solumedrol, cyclosporin, azathioprine and thalidomide. If skin lesions do become infected, antibiotics may be prescribed.

Myasthenia Gravis

Myasthenia gravis (MG) is a neuromuscular disease leading to fluctuating muscle weakness and fatiguability. It is an autoimmune disorder in which weakness is caused by circulating antibodies that block acetylcholine receptors at the post-synaptic neuromuscular junction, inhibiting the stimulative effect of the neurotransmitter acetylcholine. Some autoantibodies impair the ability of acetylcholine to bind to receptors. Others lead to the destruction of receptors, either by complement fixation or by inducing the muscle cell to eliminate the receptors through endocytosis. The hallmark of myasthenia gravis is fatiguability. Muscles become progressively weaker during periods of activity and improve after periods of rest. Muscles that control eye and eyelid movement, facial expression, chewing, talking, and swallowing are especially susceptible. The muscles that control breathing and neck and limb movements can also be affected. In myasthenic crisis a paralysis of the respiratory muscles occurs, necessitating assisted ventilation to sustain life. MG is therapeutically treated with cholinesterase inhibitors (e.g., endrophonium pyridostigmine, neostigmine, etc.) or immunosuppressants (e.g., azathioprine, cyclosporine, etc.), and, in selected cases, thymectomy. High doses of corticosteroids (e.g., prednisone, methylprednisolone, etc.) are commonly used to suppress autoimmunity. Bronchodilators (e.g., albuterol, salbutamol, ipratropium, glycopyrrolate, etc.) may be useful in overcoming the bronchospasm associated with a cholinergic crisis.

Hashimoto's Thyroiditis

Hashimoto's thyroiditis (HT) or chronic lymphocytic thyroiditis is an autoimmune disease where T-cells attack thyroid tissue. Although the underlying specifics of the immune system destruction of thyroid cells is not clearly understood, various autoantibodies have been identified in HT patients, including antibodies against thyroid peroxidase, thyroglobulin and TSH receptors. Physiologically, these autoantibodies cause gradual destruction of follicles in the thyroid gland. Symptoms of Hashimoto's thyroiditis may include hypothyroidism, weight gain, depression, mania, fatigue, panic attacks, bradycardia, tachycardia, high cholesterol, reactive hypoglycemia, constipation, migraines, memory loss, infertility and hair loss. The treatment of choice for HT is thyroid hormone replacement, and the most frequently administered drug is levothyroxine sodium, usually for the lifetime of the patient. The goal of therapy is to restore a clinically and biochemically euthyroid state. One popular treatment is the combined use of liothyronine and levothyroxine in an effort to mimic more closely thyroid hormone physiology.

Graves' Disease

Graves' disease (also known as Basedow's disease or Graves-Basedow disease; GD) is a thyroid disorder characterized by goiter, exophthalmos, "orange-peel" skin, and hyperthyroidism. This disease is caused by an antibody-mediated autoimmune reaction against the receptor for thyroid-stimulating hormone, thyroglobulin and to thyroid hormones, but the trigger for this reaction is still unknown. These antibodies cause hyperthyroidism because they bind to the TSH receptor causing chronic activation. The TSH receptor is expressed on the follicular cells of the thyroid gland, and the result of chronic stimulation is an abnormally high production of thyroid hormones (T3 and T4). This in turn causes the clinical symptoms of hyperthyroidism, and the enlargement of the thyroid gland visible as goiter. Autoantibodies bind to the extraocular muscles and cause swelling behind the eyeball. The "orange peel" skin has been explained by the infiltration of antibodies under the skin, causing an inflammatory reaction and subsequent fibrous plaques. Most GD patients are treated with antithyroid agents, such as thioamides (e.g., propylthiouracil and methimazole), which inhibit iodide organification and coupling processes to prevent synthesis of thyroid hormones. Other therapeutics for GD include beta-adrenergic blockers (e.g., propranolol, atenolol, metoprolol, etc.), iodines (e.g., potassium iodide; lugol solution, diatrizoate sodium, iopanoic acid, etc.), bile acid sequestrants (e.g., cholestyramine, etc.), antiarrhythmics (e.g., amiodarone, etc.), and glucocorticoids (e.g., prednisone, methylprednisolone, dexamethasone, etc).

Addison's Disease

Addison's disease (also known as chronic adrenal insufficiency, hypocortisolism or hypocorticism) is a rare endocrine disorder in which the adrenal gland produces insufficient amounts of steroid hormones (glucocorticoids and often mineralocorticoids). It may develop in children as well as adults, and may occur as the result of a large number of underlying causes. Autoimmune destruction of the adrenal cortex (often due to antibodies against the enzyme 21-Hydroxylase) is a common cause of Addison's in teenagers and adults. This may be isolated or in the context of autoimmune polyendocrine syndrome (APS type 1 or 2). The most common symptoms are fatigue, muscle weakness, weight loss, vomiting, diarrhea, headache, sweating, changes in mood and personality and joint and muscle pains. An "Addisonian crisis" or "adrenal crisis" is a constellation of symptoms that indicate severe adrenal insufficiency and can be fatal if untreated. Characteristic symptoms of Addisonian crisis include: sudden penetrating pain in the legs, lower back, or abdomen; severe vomiting and diarrhea, resulting in dehydration; low blood pressure; loss of consciousness/Syncope; hypoglycemia; confusion; psychosis; severe lethargy; and convulsions. Treatment of Addison's disease involves replacing, or substituting, the hormones that the adrenal glands are not producing. Cortisol is replaced orally with hydrocortisone tablets, a synthetic glucocorticoid, taken once or twice a day. If aldosterone is also deficient, it is replaced with oral doses of a mineralocorticoid called fludrocortisone acetate, which is taken once a day. During an Addisonian crisis, low blood pressure, low blood glucose, and high levels of potassium can be life threatening. Standard therapy involves intravenous injections of hydrocortisone, saline, and dextrose.

Inflammatory Eye Disease

In some embodiments, regulatory T cells generated by the methods of the disclosure and/or SAP agonists may be used to treat, prevent, or reduce the severity of an inflammatory eye disease. (See, e.g., Sugita et al. Invest Ophthalmol Vis Sci 2009; Sugita et al. J Immuno. 183(8): 5013-22, 2009; Gregerson et al. J Immunol. 183(2) 814-22, 2009; Matta et al. Am J Pathol. 173(5): 1440-54, 2008; Siemasko et al. Invest Ophthalmol Vis Sci. 49(12): 5434-40, 2008; Caspi, R. Immunol Res. 42(1-3): 41-50, 2008; Nanke et al. Mod Rheumatol. 18(4): 354-8, 2008; Agarwal et al. J Immunol. 180(8): 5423-9, 2008; Ng et al. Invest Ophthalmol Vis Sci. 48(11): 5122-7, 2007; and Silver et al. J. Immunol. 179(8): 5146-58, 2007). In particular, regulatory T cells generated by the methods of the disclosure and/or SAP agonists may be used to treat, prevent, or reduce the severity of uveitis and/or uveoretinitis. (See, e.g., Commodaro et al. Invest Ophthalmol Vis Sci. 2009; Sun et al. Invest Ophthalmol Vis Sci. 51(2): 816-21, 2010; Yeh et al. Arch Ophthalmol, 127(4): 407-13, 2009; and Ke et al. Invest Ophalmol Vis Sci. 49(9): 3999-4007). For example, compositions of the disclosure may be used to treat granulamatomatous anterior uveitis, resulting from an infection (e.g., HSV, VZV, etc.), cancer, or autoimmune disorder (e.g., Wegener's granulomatosis); nongranulomatous anterior uveitis, particularly in association with keratitis, scleritis, iris atrophy, Arthralgia, or cancer; intermediate uveitis, resulting from infection, cancer, juvenile rheumatoid arthritis, multiple sclerosis, sarcoidosis, pars planitis, vitritis, or peripheral uveitis; posterior uveitis, particularly in association with retinal hemorrhage, neurosensory retinal detachment, focal retinitis, optic disc edema, or retinal vasculitis; or complications resulting from uveitis (e.g., retinal detachment, choroidal detachment, vitreous opacification, glaucoma, calcific band-shaped keratopathy, or cataracts). In certain aspects, regulatory T cells generated by the methods of the disclosure and/or SAP agonists may be used to treat, prevent, or reduce the severity of dry eye diseases including, for example, aqueous tear deficiency (e.g., Sjogrens), evaporative tear production dysfuction (e.g., sarcoid), as well as structural and exogenous disorders (e.g., limpic keratoconjunctivitis). (See, e.g., Chauhan et al. J Immunol. 182(3): 1247-52, 2009). In certain aspects, regulatory T cells generated by the methods of the disclosure and/or SAP agonists may be used to treat, prevent, or reduce the severity of allergic conjunctivitis disorders. (See, e.g., Sumi et al. Int Arch Allergy Immunol. 148(4): 305-10, 2009; Niederkorn J. Curr Opin Allergy Clin Immunol. 8(5): 472-6, 2008; and Fukushima et al. Allergol Int. 57(3): 241-6, 2008). In certain aspects, regulatory T cells generated by the methods of the disclosure and/or SAP agonists may be used to treat, prevent, or reduce the severity of inflammatory eye diseases associated with corneal transplant. (See, e.g., Jin et al. Invest Ophthalmol vis Sci. 51(2): 816-21, 2010; and Chauhan et al. J Immunol. 182(1): 143-53, 2009). In certain aspects, regulatory T cells generated by the methods of the disclosure and/or SAP agonists may be used to treat, prevent, or reduce the severity of an inflammatory eye disease associated with a neoplastic disorder. In certain aspects, regulatory T cells generated by the methods of the disclosure and/or SAP agonists may be used to treat, prevent, or reduce the severity of an inflammatory eye disease associated with a congenital disorder Autoimmune Therapeutics SAP Agonists One aspect of the disclosure provides SAP agonists useful in the treatment of various disorders, in particular, autoimmune disorders. SAP agonists encompass all compounds and compositions that increase or otherwise mimic endogenous SAP signaling, including compounds that increase SAP activity.

(i) Human Serum Amyloid P

In certain embodiments, an SAP signaling agonist is an SAP polypeptide or variant thereof. In certain embodiments, an SAP polypeptide is SAP comprising five human SAP protomers (SEQ ID NO: 1). The term "SAP protomer" is intended to refer to a polypeptide that is at least 60%, at least 70%, at least 80%, at least 85%, at least 90%, at least 95%, at least 97%, at least 99% or 100% identical to human SAP protomer, as determined using the FASTDB computer program based on the algorithm of Brutlag et al. (*Comp. App. Biosci.*, 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05. The term "SAP protomer" encompasses functional fragments and fusion proteins comprising any of the preceding. Generally, an SAP protomer will be designed to be soluble in aqueous solutions at biologically relevant temperatures, pH levels and osmolarity. The protomers that non-covalently associate together to form SAP may have identical amino acid sequences and/or post-translational modifications or, alternatively, individual protomers may have different sequences and/or modifications.

Some aspects of the invention provide polypeptides, or provide therapeutic methods for employing those polypeptides, wherein said polypeptides are defined, at least in part, to a reference sequence. Accordingly, such polypeptides may have a certain percentage of amino acid residues which are not identical to a reference sequence. In some embodiments, the non-identical residues have similar chemical properties to the residues to which they are not identical. Groups that have similar properties include the following amino acids: E, D, N, and Q; H, K, and R; Y, F and W; I, L, V, M, C, and A; and S, T, C, P, and A.

In some embodiments, the residues that are not identical are those that are not evolutionarily conserved between the reference sequence and an orthologous sequence in at least one evolutionarily related species, such as in species within the same order. In the case of a vertebrate reference sequence, the amino acids that may be mutated in a preferred embodiment are those that are not conserved between the reference sequence and the orthologous sequence in another vertebrate species. For example, if a polypeptide used in a method of the present invention is said to comprise an amino acid sequence that is at least 95% identical to human SAP (SEQ ID NO:1), then said polypeptide may have non-identical residues to those positions in which the human SAP and that of another vertebrate differ. FIG. 1 depicts human SAP aligned against two mammalian and one avian SAP sequence. Unshaded residues indicate residues that differ from the human SAP sequence.

Polypeptides sharing at least 95% identity with SEQ ID NO:1 include polypeptides having conservative substitutions in these areas of divergence. Typically seen as conservative substitutions are the replacements, one for another, among the aliphatic amino acids Ala, Val, Leu, and Ile, interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Additional guidance concerning which amino acid changes are likely to be phenotypically silent can be found in Bowie et al., Science 247:1306-1310 (1990).

SAP polypeptides typically comprise polymers that are at least 60%, at least 70%, at least 80%, at least 85%, at least 90%, at least 95%, at least 97%, or at least 99% identical to SEQ ID NO. 1.

In some embodiments, pharmaceutical compositions are provided comprising SAP, or a functional fragment thereof. In some embodiments, pharmaceutical compositions are provided comprising an SAP variant. The amino acid sequence of a SAP variant may differ from SEQ ID NO: 1 by one or more conservative substitutions. As used herein, "conservative substitutions" are residues that are physically or functionally similar to the corresponding reference residues, i.e., a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. Additional guidance concerning which amino acid changes are likely to be phenotypically silent can be found in Bowie et al., Science 247:1306-1310 (1990).

Variants and fragments of SAP that retain biological function are useful in the pharmaceutical compositions and methods described herein. In some embodiments, a variant or fragment of SAP binds FcγRI, FcγRIIA, and/or FcγRIIIB In some embodiments, a variant or fragment of SAP is used to treat or prevent and autoimmune disorder or condition.

In specific embodiments of the present invention, compositions containing SAP, SAP variants, or SAP functional fragments may be operable to raise SAP concentration in target locations to approximately at least 0.5 µg/ml. A functional fragment of SAP is a portion of the SAP polypeptide that retains native SAP activity. In humans, $^{125}$I radio-labeled SAP has been previously administered to study patients with amyloidosis. In the treatments, approximately 600 µg of SAP was administered to an adult human. Accordingly, administration of approximately 600 µg of SAP systemically to an adult human is safe. Higher dosages may also be safe under appropriate conditions.

(ii) Anti-FcγR Antibodies as SAP Agonists

In one aspect of the invention, one or more compounds are provided that mimic SAP signaling. In some embodiments, the SAP signaling agonists are anti-FcγR antibodies, wherein the antibodies are selected from a class of anti-FcγRI, anti-FcγRIIA, and anti-FcγRIII antibodies that are able to bind to either FcγRI, FcγRIIA, or FcγRIII, respectively. Anti-FcγR antibodies are IgG antibodies that bind to receptors for the Fc portion of IgG antibodies (FcγR). The anti-FcγR antibodies bind through their variable region, and not through their constant (Fc) region. Anti-FcγR antibodies may include any isotype of antibody. The anti-FcγR antibodies may be further cross-linked or aggregated with or without additional antibodies or other means. This process initiates intracellular signaling events consistent with FcγR activation. In some embodiments, the SAP signaling agonist may be a cross-linked FcγR.

Compositions containing anti-FcγRI antibodies, anti-FcγRII antibodies, and/or anti-FcγRIII antibodies may be used to suppress hypersensitive disorders in inappropriate locations.

In specific embodiments, compositions containing approximately 1.0 µg/mL anti-FcγR antibodies may be effective to inhibit autoimmune disorders by approximately 50%. In other embodiments, compositions may contain an amount sufficient to deliver 1.0 µg/mL anti-FcγR antibodies to the target tissue.

Anti-FcγR antibodies may be administered in a dose of approximately 1.0 µg/mL, in an amount sufficient to deliver 1.0 µg/mL anti-FcγR antibodies to the target tissue, or in another dose sufficient to inhibit autoimmune disorders without causing an undesirable amount of cell death in the patient.

(iii) Aggregated Fc Domains and Fc-Containing Antibodies

In some embodiments, the SAP signaling agonists are cross-linked or aggregated IgG. Cross-linked or aggregated IgG may include any IgG able to bind the target FcγR through its Fc region, provided that at least two such IgG antibodies are physically connected to one another.

Cross-linked or aggregated IgG may include whole antibodies or a portion thereof, preferably the portion functional in suppression of autoimmune disorders. For example, they may include any antibody portion able to cross-link FcγR. This may include aggregated or cross-linked antibodies or fragments thereof, such as aggregated or cross-linked whole antibodies, F(ab')$_2$ fragments, and possible even Fc fragments.

Aggregation or cross-linking of antibodies may be accomplished by any known method, such as heat or chemical aggregation. Any level of aggregation or cross-linking may be sufficient, although increased aggregation may result in increased autoimmune disorder suppression. Antibodies may be polyclonal or monoclonal, such as antibodies produced from hybridoma cells. Compositions and methods may employ mixtures of antibodies, such as mixtures of multiple monoclonal antibodies, which may be cross-linked or aggregated to like or different antibodies.

Compositions containing cross-linked or aggregated IgG may be used to suppress the autoimmune disorders in inappropriate locations.

In other specific embodiments, compositions may contain as little as 0.1 µg/ml cross-linked or aggregated IgG. Aggregated or cross-linked IgG may be administered in an amount sufficient to deliver at least 0.1 µg/ml IgG to the target tissue, or in another dose sufficient to inhibit autoimmune disorders without causing an undesirable amount of cell death in the patient.

(iv) SAP Peptidomimetic

In certain embodiments, the SAP agonists include peptidomimetics. As used herein, the term "peptidomimetic" includes chemically modified peptides and peptide-like molecules that contain non-naturally occurring amino acids, peptoids, and the like. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of SAP polypeptides.

(v) Increase SAP Activity

In some embodiments, an SAP agonist increases SAP activity. SAP activity can be increased by increasing the concentration of SAP by, for example, increasing SAP transcription, increasing translation, increasing SAP secretion, increasing SAP RNA stability, increasing SAP protein stability, or decreasing SAP protein degradation. SAP activity can also be increased by increasing specifically the "free concentration" of SAP, or rather the unbound form by, for example, decreasing SAP endogenous binding partners.

(iv) FcγR Crosslinkers

In some embodiments, fibronectin based scaffold domain proteins may be used as SAP agonists to crosslink FcγRs. Fibronectin based scaffold domain proteins may comprise a fibronectin type III domain (Fn3), in particular a fibronectin type III tenth domain ($^{10}$Fn3).

In order to crosslink FcγRs, multimers of FcγR binding Fn3 domains may be generated as described in U.S. Pat. No. 7,115,396.

Fibronectin type III (Fn3) domains comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. The BC, DE, and FG loops are both structurally and functionally analogous to the complementarity-determining regions (CDRs) from immunoglobulins Fn3 domains can be designed to bind almost any compound by altering the sequence of one or more of the BC, DE, and FG loops. Methods for generating specific binders have been described in U.S. Pat. No. 7,115,396, disclosing high affinity TNFα binders, and U.S. Publication No. 2007/0148126, disclosing high affinity VEGFR2 binders. An example of fibronectin-based scaffold proteins are Adnectins™ (Adnexus, a Bristol-Myers Squibb R&D Company).

In some embodiments, the SAP agonist is an aptamer. In order to crosslink FcγRs, multimers of FcγR binding aptamers may be generated.

Aptamers are oligonucleotides, which can be synthetic or natural, that bind to a particular target molecule, such as a protein or metabolite. Typically, the binding is through interactions other than classic Watson-Crick base pairing. Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), Gene 137(1): 25-31; Jenison, et al. (1998), Antisense Nucleic Acid Drug Dev. 8(4): 265-79; Bell, et al. (1999), In vitro Cell. Dev. Biol. Anim 35(9): 533-42; Watson, et al. (2000), Antisense Nucleic Acid Drug Dev. 10(2): 63-75; Daniels, et al. (2002), Anal. Biochem. 305(2): 214-26; Chen, et al. (2003), Proc. Natl. Acad. Sci. U.S.A. 100(16): 9226-31; Khati, et al. (2003), J. Virol. 77(23): 12692-8; Vaish, et al. (2003), Biochemistry 42(29): 8842-51).

Aptamers have a number of attractive characteristics for use as therapeutics. In addition to high target affinity and specificity, aptamers have shown little or no toxicity or immunogenicity in standard assays (Wlotzka, et al. (2002), Proc. Natl. Acad. Sci. U.S.A. 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75).

A suitable method for generating an aptamer to a target of interest is with the process entitled "Systematic Evolution of Ligands by EXponential Enrichment" ("SELEX™"). The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX™ method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule. Systematic Evolution of Ligands by Exponential Enrichment, "SELEX™," is a method for making a nucleic acid ligand for any desired target, as described, e.g., in U.S. Pat. Nos.

5,475,096 and 5,270,163, and PCT/US91/04078, each of which is specifically incorporated herein by reference.

In some embodiments, SAP agonists are Nanobodies®. Nanobodies® are antibody-derived therapeutic proteins that contain the unique structural and functional properties of naturally-occurring heavy-chain antibodies. The Nanobody® technology was originally developed following the discovery that camelidae (camels and llamas) possess fully functional antibodies that lack light chains. These heavy-chain antibodies contain a single variable domain (VHH) and two constant domains (CH2 and CH3) Importantly, the cloned and isolated VHH domain is a stable polypeptide harbouring the full antigen-binding capacity of the original heavy-chain antibody. These newly VHH domains with their unique structural and functional properties form the basis of a new generation of therapeutic antibodies.

Pharmaceutical Preparations and Formulations

In some embodiments, the present invention provides a pharmaceutical composition comprising at least one SAP glycovariant in a formulation that is suitable for administration to a patient in need thereof. The T cell population for use in the composition may be generated by the methods described herein. In some embodiments, at least 70, 80, 90, or 100% of the cells of the composition are regulatory T cells.

In some embodiments, the pharmaceutical compositions comprise at least one SAP glycovariant in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives. In some embodiments, the pharmaceutical compositions are suitable for treating or preventing an autoimmune disorder in a human subject.

In some embodiments, the composition of the present invention contains a therapeutically effective amount of regulatory T cells in combination with an effective amount of one or more active agents. In certain aspects, the active agent comprises at least one cytokine (e.g., IL-2, IL-4, IL-10, TGF-β, and/or IL-15). In certain aspects, the active agent is one or more SAP agonists. In certain embodiments, the additional active agent is a therapeutic agent used to treat autoimmune diseases.

The pharmaceutical composition comprising regulatory T cells is administered to a subject in need thereof in a manner appropriate to the disease to be treated and/or prevented. The dosage and frequency of administration will be determined by such factors as the condition of the patient and the type and/or severity of the patient's disease. Appropriate dosages may also be determined by clinical trials. An "effective amount" of the composition can be determined by a physician with consideration of individual differences in age, weight, disease severity, condition of the patient, route of administration and any other factors relevant to treatment of the patient. In general, a pharmaceutical composition comprising T regulatory cells may be administered at a dosage of about $10^4$ to $10^9$ cells/kg body weight, including all integer values within these ranges. The compositions of the invention may also be administered multiple times at these dosages. The optimal dosage and treatment regime for a particular patient can readily be determined by one skilled in the art of medicine by monitoring the patient for signs of disease and adjusting the treatment accordingly.

The cells can be administered by using infusion techniques that are commonly used in immunotherapy, and may be administered to a patient subcutaneously, intradermally, intramuscularly, or by intravenous injection (see, e.g., Rosenburg et al., New Eng. J. Med.). Compositions of the present invention are preferably formulated for intravenous administration.

In certain embodiments, the methods described herein involve administration of an anti-autoimmune therapy to a subject. The therapeutic agents may be formulated in a conventional manner using one or more physiologically acceptable carriers or excipients. For example, therapeutic agents and their physiologically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, therapeutic agents may be administered locally, at the site where the target cells are present, i.e., in a specific tissue, organ, or fluid (e.g., blood, cerebrospinal fluid, tumor mass, etc.).

Therapeutic agents can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included. In some embodiments, the therapeutic agents can be administered to cells by a variety of methods know to those familiar in the art, including, but not restricted to, encapsulation in liposomes, by iontophoresis, or by incorporation into other vehicles, such as hydrogels, cyclodextrins, biodegradable nanocapsules, and bioadhesive microspheres.

For oral administration, the pharmaceutical compositions may take the form of, for example, tablets, lozenges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), therapeutic agents may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

In the methods of the invention, the pharmaceutical compounds can also be administered by intranasal or intrabronchial routes including insufflation, powders, and aerosol formulations (for examples of steroid inhalants, see Rohatagi (1995) J. Clin. Pharmacol. 35:1187-1193; Tjwa (1995) Ann Allergy Asthma Immunol. 75:107-111). For example, aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer Typically, such administration is in an aqueous pharmacologically acceptable buffer.

Therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition, therapeutic agents may also be formulated as a depot preparation. Such long acting formulations may be administered by implantation (for example subcutaneously or intramuscularly) or by intramuscular injection. Thus, for example, therapeutic agents may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the blood-brain-barrier in an attempt to exploit one of the endogenous transport pathways of the blood-brain-barrier; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

In certain embodiments, therapeutic agents are incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical compositions (including cosmetic preparations) may comprise from about 0.00001 to 100% such as from 0.001 to 10% or from 0.1% to 5% by weight of one or more Therapeutic agents described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of therapeutic agents, or by insertion of a sustained release device that releases therapeutic agents. Therapeutic agents may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, conjunctiva, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds may be injected directly into the vitreous and aqueous humour. In a further alternative, the compounds may be administered systemically, such as by intravenous infusion or injection, for treatment of the eye.

Therapeutic agents described herein may be stored in oxygen-free environment according to methods in the art.

Methods for delivering nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

Antisense nucleotides, such as siRNA, may be delivered to cancer cells using a variety of methods. Cell-penetrating peptides (CPPs) having the ability to convey linked "cargo" molecules into the cytosol may be used (see Juliano, Ann N Y Acad Sci. 2006 October; 1082:18-26). In certain embodiments, an atelocollagen-mediated oligonucleotide delivery system is used (Hanai et al. Ann N Y Acad Sci. 2006 October; 1082:9-17). An LPD formulation (liposome-polycation-DNA complex) may be used to deliver siRNA to tumor cells. (Li et al. Ann N Y Acad Sci. 2006 October; 1082:1-8). Complexation of siRNAs with the polyethylenimine (PEI) may also be sued to deliver siRNA into cells (Aigner, J Biomed Biotechnol. 2006; 2006(4):71659). siRNA may also be complexed with chitosan-coated polyisohexylcyanoacrylate (PIHCA) nanoparticles for in vivo delivery. (Pille et al., Hum Gene Ther. 2006 October; 17(10):1019.

The present invention further provides use of any agent identified by the present invention in the manufacture of a medicament for the treatment or prevention of an autoimmune disorder or a condition in a patient, for example, the use of an SAP agonist in the manufacture of medicament for the treatment of an autoimmune disorder or condition. In some aspects, any agent identified by the present invention may be used to make a pharmaceutical preparation for the use in treating or preventing an autoimmune disease or condition.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.
Exemplification Example 1

Chronic allergic airway disease induced by *A. fumigatus* conidia is characterized by airway hyperreactivity, lung inflammation, eosinophilia, mucus hypersecretion, goblet cell hyperplasia, and subepithelial fibrosis. C57BL/6 mice were similarly sensitized to a commercially available preparation of soluble *A. fumigatus* antigens as previously described (Hogaboam et al. The American Journal of Pathology. 2000; 156: 723-732). Seven days after the third intranasal challenge, each mouse received $5.0 \times 10^6$ *A. fumigatus* conidia suspended in 30 µl of PBS tween 80 (0.1%, vol/vol) via intratracheal route.

Figure 2B:
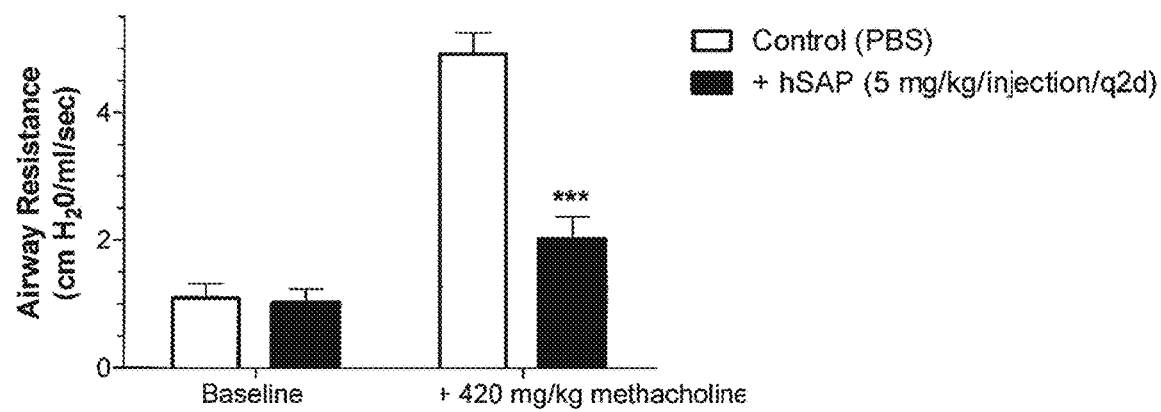

At day 15- and 30-time points (FIGS. 2A and 2B respectively), groups of five mice treated with SAP or control (PBS) were analyzed for changes in airway hyperresponsiveness (AHR). Bronchial hyperresponsiveness was assessed after an intratracheal *A. fumigatus* conidia challenge using a Buxco™ plethysmograph (Buxco, Troy, N.Y.). Briefly, sodium pentobarbital (Butler Co., Columbus, Ohio; 0.04 mg/g of mouse body weight) was used to anesthetize mice prior to their intubation and ventilation was carried out with a Harvard pump ventilator (Harvard Apparatus, Reno Nev.). Once baseline airway resistance was established, 420 mg/kg of methacholine was introduced into each mouse via cannulated tail vein, and airway hyperresponsiveness was monitored for approximately 3 minutes. The peak increase in airway resistance was then recorded. At day 15- and 30-time points (FIGS. 2A and 2B respectively), groups of five mice treated with SAP or control (PBS) were anesthetized with sodium pentobarbital and analyzed for changes in AHR. SAP significantly reduced the amount of AHR in response to intravenous methacholine challenge.

Example 2

C57BL/6 mice were similarly sensitized to a commercially available preparation of soluble *A. fumigatus* antigens as above described. Animals were treated in vivo with hSAP or PBS control for the last two weeks of the model. At day 15- and 30-time points (FIGS. 3A and 3B respectively), groups of five mice treated were analyzed for changes in cytokine production. Spleen cells were isolated from animals at 15 or 30 days after intratracheal conidia challenge, stimulated with aspergillus antigen, and treated in vitro with hSAP. Splenocyte cultures were quantified (pg/mL) for production of IL-4, IL-5, and INF-γ.

Example 3

Figure 4:
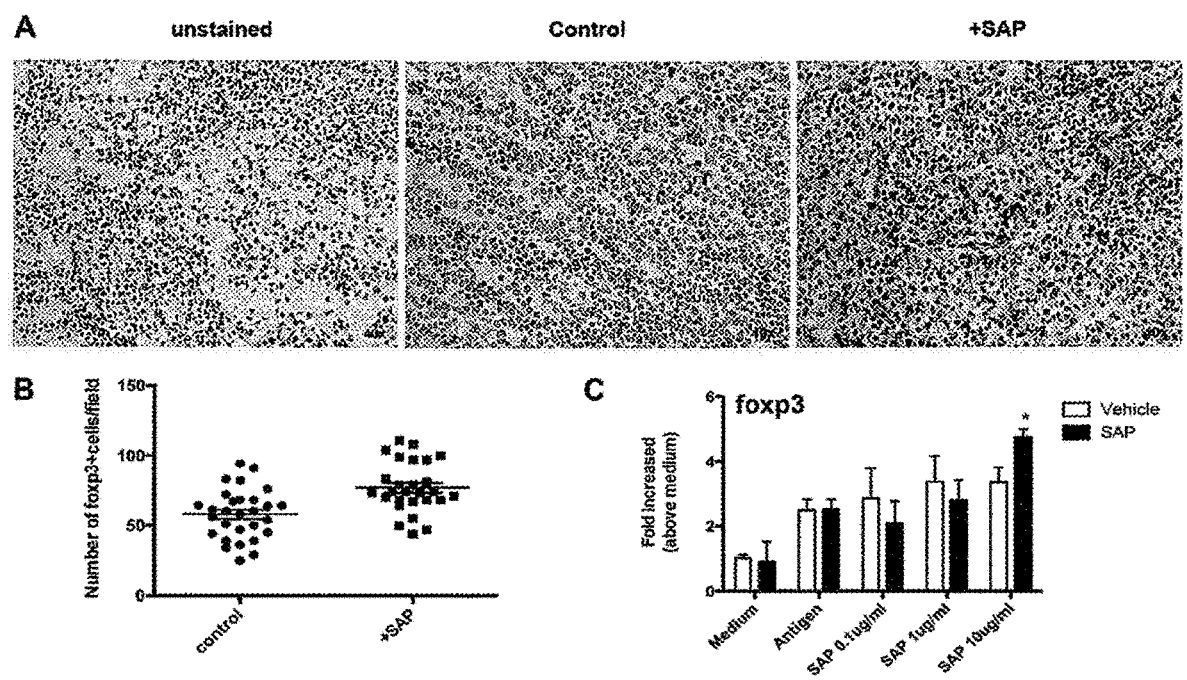
FIG. 4. FoxP3 Expression in pulmonary draining lymph nodes (A and B) or splenocyte cultures (C). A and B are from draining lymph nodes from the lung taken at day 15 from animals treated with PBS (control), or animals treated with SAP (+SAP) and stained for FoxP3. C is from splenocyte cultures that were stimulated with *Aspergillus* antigen in vitro in the presence or absence of SAP in vitro (0.1-10 μg/ml) for 24 hours. Total FoxP3 expression was quantitated using real time RT-PCR.

C57BL/6 mice were similarly sensitized to a commercially available preparation of soluble *A. fumigatus* antigens as above described. At day 15, the amount of FoxP3 expression was determined in pulmonary draining lymph nodes or splenocyte cultures. Pulmonary lymph nodes were dissected from each mouse and snap frozen in liquid $N_2$ or fixed in 10% formalin for histological analysis. Histological samples from animals treated with PBS (control) or SAP were stained for FoxP3 (FIG. 4A), and the number of FoxP3+ cells were quantified relative to each field examined (FIG. 4B). Purified splenocyte cultures were stimulated with *Aspergillus* antigen in vitro in the presence or absence of SAP in vitro (0.1-10 µg/ml) for 24 hours. Total FoxP3 expression was quantitated using real time RT-PCR (FIG. 4C).

Example 4

Figure 5:
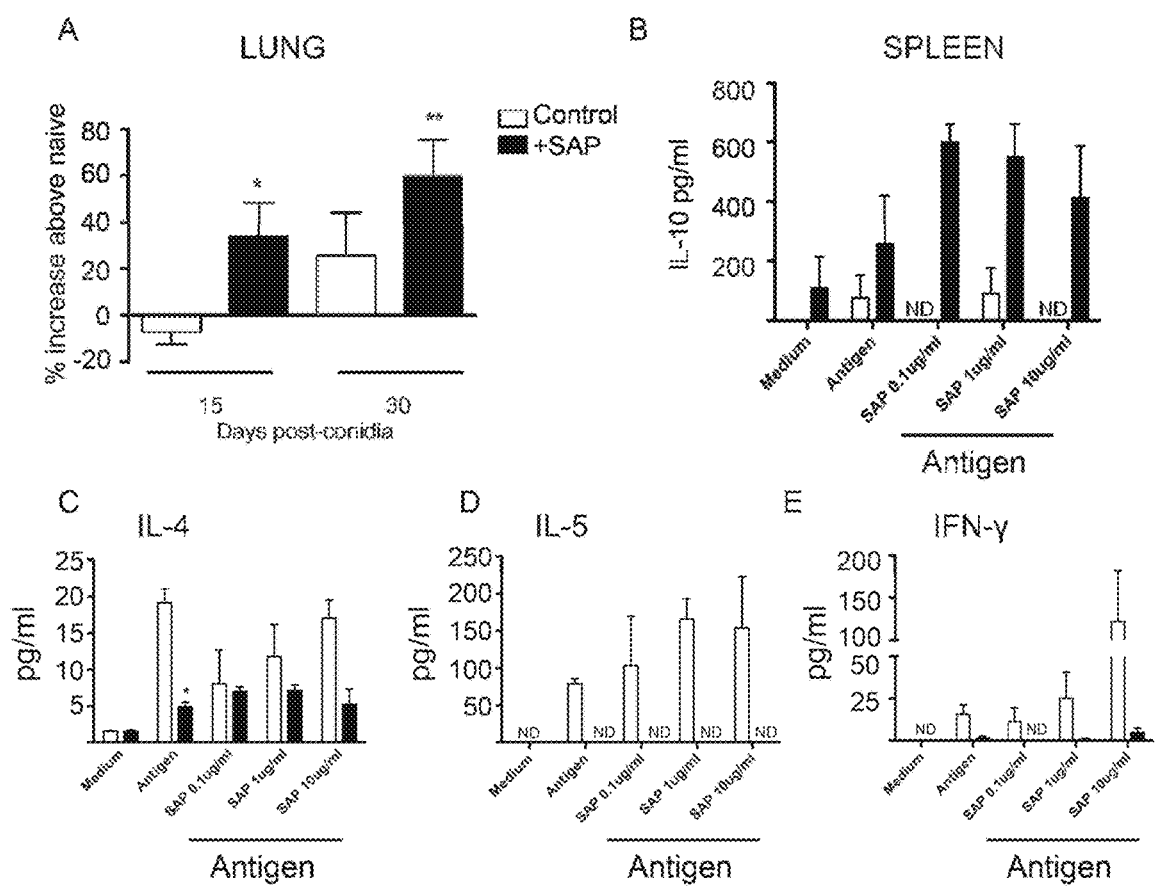
FIG. 5. Effects of SAP in vivo and in vitro on IL-10 and antigen recall. Mice were sensitized and challenged with *Aspergillus fumigatus* in vivo and treated with control (PBS, i.p., 2qd, open bars) or SAP (5 mg/kg, i.p. q2d, filled bars) on days 15-30 post-live conidia challenge. At day 30 mice were killed, A. total lung IL-10 was measured by luminex, B-E. Splenocyte cultures were stimulated in vitro with *Aspergillus fumigatus* antigen, in the presence or absence of SAP and cell-free supernatants assessed for B. IL-10, C. IL-4, D. IL-5 and E. IFN-γ protein levels by specific ELISA. Animals treated with SAP (i.p., 2qd on days 15-30) had enhanced levels of IL10 in the lungs in comparison to animals treated with PBS (i.p., q2d, on days 15-30) and compared to native, non-allergic lung. Further there was a diminished antigen recall response, indicating enhanced T regulatory cell number and/or function.

The effects of SAP in vivo and in vitro on IL-10 and antigen recall were examined. Mice were sensitized and challenged with *Aspergillus fumigatus* in vivo and treated with control (PBS, i.p., open bars) or SAP (5 mg/kg, ip.p q2d, filled bars) on days 15-30 post-live conidia challenge. At day 30, mice were sacrificed. A) Total lung IL-10 was measured by luminex. B-E) Single cell splenocyte cultures were stimulated in vitro with *Aspergillus fumigatus* antigen, in the presence or absence of SAP (FIG. 5). Cell-free supernatants were assessed for B) IL-10, C) IL-4, D) IL-5 and E) IFN-γ protein levels by ELISA. The data demonstrates that SAP treated animals (i.p., q2d on days 15-30) had enhanced levels of IL-10 in the lungs in comparison to asthma control (PBS, q2d, on days 15-30) and levels were comparable to that in naive, non-allergic lung (FIG. 5). Splenocytes from SAP treated mice have a reduced Th1 or Th2 antigen recall response and increased IL-10. As there is also an increase in FoxP3 expression, this data indicates that SAP induces regulatory T cells within the setting of allergic airways disease.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the below listed claims. The full scope of the invention should be determined by reference to the claims, along with their full scope of equivalents, and the specification, along with such variations.

I claim:

1. A method of increasing expression of IL-10 and the number of FoxP3+ cells in a patient having multiple sclerosis, the method comprising administering to the patient an amount of a serum amyloid P (SAP) protein comprising the amino acid sequence set forth in SEQ ID NO: 1 effective to increase the number of FoxP3+ cells in the patient.

2. The method of claim 1, wherein the subject is a human.

3. The method of claim 1, wherein the SAP protein is formulated in a liquid solution.

* * * * *

UNITED STATES PATENT AND TRADEMARK OFFICE
CERTIFICATE OF CORRECTION

PATENT NO. : 10,702,583 B2
APPLICATION NO. : 12/720845
DATED : July 7, 2020
INVENTOR(S) : Murray Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*

```
                              SEQUENCE LISTING

<160> NUMBER OF SEQ ID NOS: 4

<210> SEQ ID NO 1
<211> LENGTH: 204
<212> TYPE: PRT
<213> ORGANISM: Homo sapiens

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
            115                 120                 125

Pro Lys Ile Val Leu Gly Gln Glu Gln Asp Ser Tyr Gly Gly Lys Phe
        130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 2
<211> LENGTH: 208
<212> TYPE: PRT
<213> ORGANISM: Gallus gallus

<400> SEQUENCE: 2

Gln Glu Asp Leu Tyr Arg Lys Val Phe Val Phe Arg Glu Asp Pro Ser
1               5                   10                  15

Asp Ala Tyr Val Leu Leu Gln Val Gln Leu Glu Arg Pro Leu Leu Asn
            20                  25                  30

Phe Thr Val Cys Leu Arg Ser Tyr Thr Asp Leu Thr Arg Pro His Ser
        35                  40                  45

Leu Phe Ser Tyr Ala Thr Lys Ala Gln Asp Asn Glu Ile Leu Leu Phe
    50                  55                  60

Lys Pro Lys Pro Gly Glu Tyr Arg Phe Tyr Val Gly Gly Lys Tyr Val
65                  70                  75                  80

Thr Phe Arg Val Pro Glu Asn Arg Gly Glu Trp Glu His Val Cys Ala
```

```
                    85                  90                  95
Ser Trp Glu Ser Gly Ser Gly Ile Ala Glu Phe Trp Leu Asn Gly Arg
                100                 105                 110

Pro Trp Pro Arg Lys Gly Leu Gln Lys Gly Tyr Glu Val Gly Asn Glu
            115                 120                 125

Ala Val Val Met Leu Gly Gln Glu Gln Asp Ala Tyr Gly Gly Gly Phe
        130                 135                 140

Asp Val Tyr Asn Ser Phe Thr Gly Glu Met Ala Asp Val His Leu Trp
145                 150                 155                 160

Asp Ala Gly Leu Ser Pro Asp Lys Met Arg Ser Ala Tyr Leu Ala Leu
                165                 170                 175

Arg Leu Pro Pro Ala Pro Leu Ala Trp Gly Arg Leu Arg Tyr Glu Ala
            180                 185                 190

Lys Gly Asp Val Val Lys Pro Arg Leu Arg Glu Ala Leu Gly Ala
        195                 200                 205

<210> SEQ ID NO 3
<211> LENGTH: 205
<212> TYPE: PRT
<213> ORGANISM: Bos Taurus

<400> SEQUENCE: 3

Gln Thr Asp Leu Arg Gly Lys Val Phe Val Phe Pro Arg Glu Ser Ser
1               5                   10                  15

Thr Asp His Val Thr Leu Ile Thr Lys Leu Glu Lys Pro Leu Lys Asn
                20                  25                  30

Leu Thr Leu Cys Leu Arg Ala Tyr Ser Asp Leu Ser Arg Gly Tyr Ser
            35                  40                  45

Leu Phe Ser Tyr Asn Ile His Ser Lys Asp Asn Glu Leu Leu Val Phe
        50                  55                  60

Lys Asn Gly Ile Gly Glu Tyr Ser Leu Tyr Ile Gly Lys Thr Lys Val
65                  70                  75                  80

Thr Val Arg Ala Thr Glu Lys Phe Pro Ser Pro Val His Ile Cys Thr
                85                  90                  95

Ser Trp Glu Ser Ser Thr Gly Ile Ala Glu Phe Trp Ile Asn Gly Lys
                100                 105                 110

Pro Leu Val Lys Arg Gly Leu Lys Gln Gly Tyr Ala Val Gly Ala His
            115                 120                 125

Pro Lys Ile Val Leu Gly Gln Glu Gln Asp Ser Tyr Gly Gly Gly Phe
        130                 135                 140

Asp Lys Asn Gln Ser Phe Met Gly Glu Ile Gly Asp Leu Tyr Met Trp
145                 150                 155                 160

Asp Ser Val Leu Ser Pro Glu Glu Ile Leu Leu Val Tyr Gln Gly Ser
                165                 170                 175

Ser Ser Ile Ser Pro Thr Ile Leu Asp Trp Gln Ala Leu Lys Tyr Glu
            180                 185                 190

Ile Lys Gly Tyr Val Ile Val Lys Pro Met Val Trp Gly
        195                 200                 205

<210> SEQ ID NO 4
<211> LENGTH: 204
<212> TYPE: PRT
<213> ORGANISM: Cricetulus migratorius

<400> SEQUENCE: 4

Gln Thr Asp Leu Thr Gly Lys Val Phe Val Phe Pro Arg Glu Ser Glu
```

-continued

```
1               5                   10                  15
Ser Asp Tyr Val Lys Leu Ile Pro Arg Leu Glu Lys Pro Leu Glu Asn
            20                  25                  30

Phe Thr Leu Cys Phe Arg Thr Tyr Thr Asp Leu Ser Arg Pro His Ser
            35                  40                  45

Leu Phe Ser Tyr Asn Thr Lys Asn Lys Asp Asn Glu Leu Leu Ile Tyr
            50                  55                  60

Lys Glu Arg Met Gly Tyr Gly Leu Tyr Ile Glu Asn Val Gly Ala
65                  70                  75                  80

Ile Val Arg Gly Val Glu Glu Phe Ala Ser Pro Val His Phe Cys Thr
                85                  90                  95

Ser Trp Glu Ser Ser Ser Gly Ile Ala Asp Phe Trp Val Asn Gly Ile
            100                 105                 110

Pro Trp Val Lys Lys Gly Leu Lys Lys Gly Tyr Thr Val Lys Thr Gln
            115                 120                 125

Pro Ser Ile Ile Leu Gly Gln Glu Gln Asp Asn Tyr Gly Gly Gly Phe
            130                 135                 140

Asp Lys Ser Gln Ser Phe Val Gly Glu Met Gly Asp Leu Asn Met Trp
145                 150                 155                 160

Asp Ser Val Leu Thr Pro Glu Glu Ile Lys Ser Val Tyr Glu Gly Ser
                165                 170                 175

Trp Leu Glu Pro Asn Ile Leu Asp Trp Arg Ala Leu Asn Tyr Glu Met
            180                 185                 190

Ser Gly Tyr Ala Val Ile Arg Pro Arg Val Trp His
            195                 200
```